US010071130B2

(12) United States Patent
Conzen

(10) Patent No.: US 10,071,130 B2
(45) Date of Patent: Sep. 11, 2018

(54) METHODS AND COMPOSITIONS RELATED TO HSP90 INHIBITORS AND BREAST CANCER

(71) Applicant: The University of Chicago, Chicago, IL (US)

(72) Inventor: Suzanne D. Conzen, Chicago, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 15/103,187

(22) PCT Filed: Dec. 12, 2014

(86) PCT No.: PCT/US2014/070032
§ 371 (c)(1),
(2) Date: Jun. 9, 2016

(87) PCT Pub. No.: WO2015/089402
PCT Pub. Date: Jun. 18, 2015

(65) Prior Publication Data
US 2016/0317601 A1 Nov. 3, 2016

Related U.S. Application Data

(60) Provisional application No. 61/915,411, filed on Dec. 12, 2013.

(51) Int. Cl.

| | | |
|---|---|---|
| *A61K 31/535* | (2006.01) | |
| *A61K 38/05* | (2006.01) | |
| *A61K 45/06* | (2006.01) | |
| *A61K 31/7048* | (2006.01) | |
| *A61K 31/337* | (2006.01) | |
| *A61K 31/4196* | (2006.01) | |
| *A61K 31/5377* | (2006.01) | |
| *A61N 5/10* | (2006.01) | |
| *C12Q 1/6886* | (2018.01) | |
| *G01N 33/574* | (2006.01) | |

(52) U.S. Cl.
CPC ............ *A61K 38/05* (2013.01); *A61K 31/337* (2013.01); *A61K 31/4196* (2013.01); *A61K 31/5377* (2013.01); *A61K 31/7048* (2013.01); *A61K 45/06* (2013.01); *A61N 5/10* (2013.01); *C12Q 1/6886* (2013.01); *G01N 33/57415* (2013.01); *G01N 33/57434* (2013.01); *G01N 33/57492* (2013.01); *G01N 2333/705* (2013.01)

(58) Field of Classification Search
USPC ..................................................... 514/229.5
See application file for complete search history.

(56) References Cited

U.S. PATENT DOCUMENTS

| 8,710,035 B2 | 4/2014 | Pan et al. ................. 514/171 |
| 2002/0115613 A1 | 8/2002 | Kumar ...................... 424/85.1 |
| 2007/0128627 A1 | 6/2007 | Simons et al. ............. 435/6.19 |
| 2007/0249540 A1* | 10/2007 | Papathanassiu ....... A61K 38/05 514/1.9 |
| 2008/0287419 A1 | 11/2008 | Bruncko et al. ........ 514/211.15 |
| 2010/0135956 A1 | 6/2010 | Gant et al. ................ 424/85.2 |
| 2011/0263693 A1* | 10/2011 | Vinson-Hieronymus ............... A61K 31/203 514/453 |
| 2011/0269728 A1 | 11/2011 | Pan et al. ................. 514/171 |
| 2011/0319415 A1* | 12/2011 | Thomas ............... C12Q 1/6886 514/236.8 |
| 2012/0022121 A1 | 1/2012 | Dalton et al. .............. 514/367 |
| 2015/0010503 A1 | 1/2015 | Szmulewitz et al. ........ 424/85.4 |

FOREIGN PATENT DOCUMENTS

| WO | WO 2012/149493 | 11/2012 |
| WO | WO 2013/075059 | 5/2013 |

OTHER PUBLICATIONS

Belova et. al. (Breast cancer Res. Treat. (2009) 116:441-447).*
"Data Sheet: Glucocorticoid Receptor mouse monoclonal antibody NCL-GCR", Novocastra Laboratories Ltd., available at http://www.ebiotrade.com/buyf/Novocastra/data/hrerp/gcr.pdf, accessed on Jun. 7, 2011.
"Identification of Glucocorticoid Receptor (GR) signatures in primary human breast cancer: Association with relapse-free survival time" poster presented by S.D. Conzen as a short talk, presented at Nuclear Receptors: Signaling, Gene Regulation and Cancer, Keystone Symposia on Molecular and Cellular Biology, Keystone Resort, Keystone, Colorado, Thursday, Mar. 25, 2010.
Arora et al., "Glucocorticoid Receptor Confers Resistance to Antiandrogens by Bypassing Androgen Receptor Blockade", *Cell*, 155:1309-0322, 2013.
Belanoff et al., "Selective glucocorticoid receptor (type II) antagonists prevent weight gain caused by olanzapine in rats," Eur. J. Pharmacol., 655(1-3):117-120, 2011.
Belova et al., "Glucocorticoid receptor expression in breast cancer associates with older patient age", *Breast Cancer Res. Treat.*, 116(3):441-447, 2009.
Bolton et al., "Cell- and gene-specific regulation of primary target genes by the androgen receptor", *Genes Dev.*, 21(16):2005-2017, 2007.
Chan et al., "Prognostic Significance of Gleason Score 3+4 versus Gleason Score 4+3 Tumor at Radical Prostatectomy", *Urology*, 56(5):823-827, 2000.
Chen et al., "Androgen and Glucocorticoid Receptor Heterodimer Formation", *J. Biol. Chem.*, 272(22):14087-14092, 1997.
Cho et al., "Role of activation function domain-1, DNA binding, and coactivator GRIP1 in the expression of partial agonist activity of glucocorticoid receptor-antagonist complexes," *Biochemistry*, 44(9):3547-3561, 2005.

(Continued)

*Primary Examiner* — Marcos L Sznaidman
(74) *Attorney, Agent, or Firm* — Norton Rose Fulbright US LLP

(57) ABSTRACT

Embodiments of the invention are directed to methods of treating cancer cells, particularly breast cancer cells, such as chemo-resistant cells, with an Hsp90 inhibitor and an anti-cancer agent or compound such as chemotherapy.

14 Claims, 9 Drawing Sheets

(56) References Cited

OTHER PUBLICATIONS

Clark et al., "1H-Pyrazolo [3,4-g] hexahydro-Isoquinolines as selective glucocorticoid receptor antagonists with high functional activity", *Bioorganic & Medicinal Chemistry Letters.*, 18: 1312-1317, 2008.
Clark, "Glucocorticoid Receptor Antagonists" Current Topics in Medicinal Chemistry, 8:813-838, 2008.
Cleutjens et al., "Both Androgen Receptor and Glucocorticoid Receptor Are Able to Induce Prostate-Specific Antigen Expression, but Differ in their Growth-Stimulating Properties of LNCaP Cells*'", *Endocrinology*, 138(12):5293-5300, 1997.
Colleoni et al., "Response to primary chemotherapy in breast cancer patients with tumors not expressing estrogen and progesterone receptors" Annals of Oncology, 11(8):1057-9, 2000.
Davies et al., "Association of glucocorticoid receptors with prostate nuclear sites for androgen receptors and with androgen response elements", *J Mol Endocrin.*, 5: 117-127, 1990.
De Bono et al., "Abiraterone and Increased Survival in Metastatic Prostate Cancer", *N. Engl. J. Med.*, 364(21):1995-2005, 2011.
Desmedt et al., "Strong Time Dependence of the 76-Gene Prognostic Signature for Node-Negative Breast Cancer Patients in the TRANSBIG Multicenter Independent Validation Series" Clin. Cancer Res., 13:3207-3214, 2007.
Donovan et al., "Androgen receptor expression is associated with prostate cancer-specific survival in castrate patients with metastatic disease", *BJU Int.*, 105(4):462-467, 2010.
Efstathiou et al., "Molecular Characterization of Enzalutamide-treated Bone Metastatic Castration-resistant Prostate Cancer", *Eur. Uro.*, 67:53-60, 2015.
Fakih et al., "Glucocorticoids and Treatment of Prostate Cancer: A Preclinical and Clinical Review", *Urology*, 60(4):553-561, 2002.
Fiorentino et al., "Blood and tissue biomarkers in prostate cancer: state of the art", *Urol. Clin. North. Am.*, 37(1):131-141, 2010.
Fradet, "Biomarkers in prostate cancer diagnosis and prognosis: beyond prostate-specific antigen", *Curr. Opin.* Urol., 19(3):243-246, 2009.
Gaddy et al., "Mifepristone Induces Growth Arrest, Caspase Activation, and Apoptosis of Estrogen Receptor-Expressing, Antiestrogen-Resistant Breast Cancer Cells", *Clin Cancer Res.*, 10: 5215-5225, 2004.
Grover and Martin, "The initiation of breast and prostate cancer" Carcinogenesis, 23(7): 1095-1102, 2002.
Guo et al., "A Novel Androgen Receptor Splice Variant Is Upregulated during Prostate Cancer Progression and Promotes Androgen-depletion-resistant Growth", *Cancer Res.*, 69(6):2305-2313, 2009.
Han et al., "Biochemical (Prostate Specific Antigen) Recurrence Probability Followig Radical Prostatectomy for Clinically Localized Prostate Cancer", *J. Urol.*, 169(2):517-523, 2003.
Hein et al., "Click Chemistry, A powerful Tool for Pharmaceutical Sciences" Pharmaceutical Research, 25(10):2216-30, 2008.
Henderson et al., "Estrogens as a cause of human cancer: the Richard and Hinda Rosenthal Foundation award lecture" Cancer Res., 48:246-253, 1988.
Ho et al., "A Complex Response Element in Intron 1 of the Androgen-regulated 20-kDa Protein Gene Displays Cell Type-dependent Androgen Receptor Specificity", *J. Biol. Chem.*, 268(36):27226-27235, 1993.
International Preliminary Report on Patentability in International Application No. PCT/US2013/027150 dated Sep. 4, 2014.
International Search Report and Written Opinion issued in PCT/US2014/070032, dated Mar. 31, 2015.
Isikbay et al., "Glucocorticoid Receptor Activity Contributes to Resistance to Androgen-Targeted Therapy in Prostate Cancer", *Horm. Canc.*, 5:72-89, 2014.
Jemal et al., "Cancer Statistics", CA Cancer J. Clin., 60(5):277-300, 2010.
Karantanos et al., "Understanding the Mechanisms of Androgen Deprivation Resistance in Prostate Cancer at the Molecular Level", *Eur. Urol.*, 67(1):470-479, 2015.

Keen and Davidson, "The biology of breast carcinoma" Cancer, 97 (3 Suppl):825-33, 2003.
Klein et al., "Analyzing survival curves at a fixed point in time", *Stat. Med.*, 26(24): 4505-4519, 2007.
Klijn et al., "Antiprogestins, a New Form of Endocrine Therapy for Human Breast Cancer", Cancer Research, 49: 2851-2856, 1989.
Koochekpour, "Androgen receptor signaling and mutations in prostate cancer", Asian J. Androl., 12(5):639-657, 2010.
Kriaucionis et al., "The nuclear DNA base 5-hydroxymethylcytosine is present in Purkinje neurons and the brain" Science, 15;324(5929):929-30, 2009.
Lehmann et al. "Identification of human triple-negative breast cancer subtypes and preclinical models for selection of targeted therapies", *Journal of Clinical Investigations*, Jul. 1, 2011, vol. 121, No. &, pp. 2750-2767.
Li et al., "High Level of Androgen Receptor Is Associated With Aggressive Clinicopathologic Features and Decreased Biochemical Recurrence-free Survival in Prostate", Am. J. Surg. Pathol., 28(7):928-934, 2004.
Loi et al., "Definition of Clinically Distinct Molecular Subtypes in Estrogen Receptor-Positive Breast Carcinomas Through Genomic Grade" Journal of Clinical Oncology, 25:1239-1246, 2006.
Loi et al., "Predicting prognosis using molecular profiling in estrogen receptor-positive breast cancer treated with tamoxifen" BMC Genomics, 9:239, 2008.
Lotan et al., "Up-regulation of MKK4, MKK6 and MKK7 during prostate cancer progression: an important role for SAPK signalling in prostatic neoplasia", *J. Pathol.*, 212(4):386-394, 2007.
Lucci, et al., "Modification of ceramide metabolism increases cancer cell sensitivity to cytotoxics." Int J Onco. 15: 541-546, 1999.
Ma et al. "IL-21 activates both innate and adaptive immunity to generate potent antitumor responses that require perforin but are independent of IFN-gamma" J. Immunol, 171(2):608-615, 2003.
Makarov et al., "Updated Nomogram to Predict Pathologic Stage of Prostate Cancer Given Prostate-Specific Antigen Level, Clinical Stage, and Biopsy Gleason Score (Partin Tables) Based on Cases from 2000 to 2005", *Urology*, 69(6):1095-1101, 2007.
Melhem et al., "Administration of glucocorticoids to ovarian cancer patients is associated with expression of the anti-apoptotic genes SGK1 and MKP1/DUSP1 in ovarian tissues" Clin. Cancer Res., 15(9):3196-204, 2009.
Mikosz et al., "Glucocorticoid receptor-mediated protection from apoptosis is associated with induction of the serine/threonine survival kinase gene, sgk-1" J. Biol. Chem., 276 (20):16649-54, 2001.
Minn et al.. "Genes that mediate breast cancer metastasis to lung". Nature 28;436(7050):518-24, 2005.
Mohler et al., "Androgen and Glucocorticoid Receptors in the Stroma and Epithelium of Prostatic Hyperplasia and Carcinoma", *Clin. Cancer Res.*, 2(5):889-895, 1996.
Montgomery et al., "Impact of Baseline Corticosteroids on Survival and Steroid Androgens in Metastatic Castration-resistant Prostate Cancer: Exploratory Analysis from COU-AA-301", *Eur. Uro.*, 2014.
Moran et al., "The glucocorticoid receptor mediates a survival signal in human mammary epithelial cells" Cancer Res., 60 (4):867-72, 2000.
Moses et al., "The growing applications of click chemistry" Chem Soc Rev., 36(8):1249-62, 2007.
Niemeier et al., "Androgen receptor in breast cancer: expression in estrogen receptor-positive tumors and in estrogen receptor-negative tumors with apocrine differentiation", *Mod. Pathol.*, 23(2): 205-212, 2010.
Pan et al., "Activation of the glucocorticoid receptor is associated with poor prognosis in estrogen receptor-negative breast cancer," Cancer Research, Published Online First Aug. 25, 2011; doi: 10.1158/0008-5472.CAN-11-0362.
Pang et al., "Dexamethasone decreases xenograft response to Paclitaxel through inhibition of tumor cell apoptosis" Cancer Biol. Ther., 5(8):933-40, 2006.
Partial Supplementary European Search Report from EP Application No. 13751132.5, dated Sep. 7, 2015.
Peeters et al., "Differential effects of the new glucocorticoid receptor antagonist ORG 34517 and RU486 (mifepristone) on

(56) References Cited

OTHER PUBLICATIONS glucocorticoid receptor nuclear translocation in the AtT20 cell line," Ann. NY Acad. Sci., 1148:536-541, 2008.

Petrylak et al., "Evaluation of Prostate-Specific Antigen Declines for Surrogacy in Patients Treated on SWOG 99-16", *J. Natl. Cancer Inst.*, 98(8):516-521, 2006.

Pike et al., "Estrogens, progestogens, normal breast cell proliferation, and breast cancer risk" Epidemiologic Rev., 15(1):17-35, 1993.

Pound et al., "Natural History of Progression After PSA Elevation Following Radical Prostatectomy", JAMA, 281(17): 1591-1597, 1999.

Rauhala et al., "Dual-specificity phosphatase 1 and serum/glucocorticoid-regulated kinase are downregulated in prostate cancer", *Int. J. Cancer*, 117(5):738-745, 2005.

Ring et al., "Mechanisms of tamoxifen resistance", *Endocrine Related Cancer*, 11: 643-658, 2004.

Robinson et al., "Octahydrophenanthrene-2, 7-diol Analogues as dissociated Glucocorticoid Receptor Agonists Discovery and Lead Exploration" J. Med. Chem.,. 52:1731-43, 2009.

Rosner et al., "Higher Tumor to Benign Ratio of the Androgen Receptor mRNA Expression Associates with Prostate Cancer Progression after Radical Prostaectomy", *Urology*, 70(6):1225-1229, 2007.

Sahoo et al., "Coordinate expression of the PI3-kinase downstream effectors serum and glucocorticoid-induced kinase (SGK-1) and Akt-1 in human breast cancer", *Eur. J. Cancer*, 41(17):2754-2759, 2005.

Sahu et al., "FoxA1 Specifics Unique Androgen and Glucocorticoid Receptor Binding Events in Prostate Cancer Cells", *Cancer Res.*, 73(5):1570-0580, 2013.

Scher and Sawyers, "Biology of Progressive, Castration-Resistant Prostate Cancer: Directed Therapies Targeting the Androgen-Receptor Signaling Axis", *J. Clin. Oncol.*, 23(32): 8253-8261, 2005.

Search Report and Written Opinion in International Application No. PCT/US2013/027150 dated Apr. 29, 2013.

Seruga et al., "Drug resistance in metastatic castration-resistant prostate cancer", *Nature Reviews Clinical Oncology*, 8: 12-23, (Jan. 2011) Epub Sep. 21, 2010.

Shanmugam et al., "Serum/glucocorticoid-induced protein kinase-1 facilitates androgen receptor-dependent cell survival", *Cell Death Differ.*, 14(12):2085-2094, 2007.

Sherk et al., "Development of a small molecule serum and glucocorticoid-regulated kinase 1 antagonist and its evaluation as a prostate cancer therapeutic", *Cancer Res.*, 68(18):7475-7483, 2008.

Sims et al., "The removal of multiplicative, systematic bias allows integration of breast cancer gene expression datasets—improving meta-analysis and prediction of prognosis" BMC Medical Genomics, 1:42, doi:10.1186/1755-8794-1-42, 2008.

Smith et al., "Expression of glucocorticoid and progesterone nuclear receptor genes in archival breast cancer tissue" Breast Cancer Res., 5(1): R9-R12, 2003.

Smith et al., "Progesterone, glucocorticoid, but not estrogen receptor mRNA is altered in breast cancer stroma" Cancer Lett., 255:77-84, 2007.

Song et al., "Dihydrotestosterone Enhances Castration-Resistant Prostate Cancer Cell Proliferation Through STAT5 Activation via Glucocorticoid Receptor Pathway", *The Prostate*, 74:1240-1248, 2014.

Sorlie et al., "Gene expression patterns of breast carcinomas distinguish tumor subclasses with clinical implications" Proc. Natl. Acad. Sci. USA, 98:10869-10874., 2001.

Sotiriou et al. "Gene expression profiling in breast cancer: understanding the molecular basis of histologic grade to improve prognosis" J. Natl. Cancer Inst, 15;98(4):262-72, 2006.

Srinivas et al., "Proteomics for cancer biomarker discovery" Clin. Chem., 48(8):1160-9, 2002.

Srivinas et al., "Phase II Study Evaluating Oral Triamcinolone in Patients With Androgen-Dependent Prostate Cancer", *Adult Urology*, 67: 1001-1006, 2006.

Stephenson et al., "Preoperative Nomogram Predicting the 10-year Probability of Prostate Cancer Recurrence After Radical Prostatectomy", *J. Natl. Cancer Inst.*, 98(10):715-717, 2006.

Sterbis et al., "Higher Expression of the Androgen-Regulated Gene PSA/HK3 mRNA in Prostate Cancer Tissues Predicts Biochemical Recurrence-Free Survival", *Clin. Cancer Res.*, 14(3):758-763, 2008.

Sun et al., "Castration resistance in human prostate cancer is conferred by a frequently occurring androgen receptor splice variant", *J. Clin. Invest.*, 120(8):2715-2730, 2010.

Szmulewitz et al., "Serum/Glucocorticoid-Regulated Kinase I Expression in Primary Human Prostate Cancers", *Prostate*, 72(2): 157-64, 2012.

Tannock et al., "Docetaxel plus Prednisone or Mitoxantrone plus Prednisone for Advanced Prostate Cancer", *N. Engl. J. Med.*, 351(15):1502-1512, 2004.

Tessier and Woodgett Jr., "Serum and Glucocorticoid-Regulated Protein Kinases: Variations on a Theme", *J. Cell Biochem.*, 98(6):1391-1407, 2006.

Wang et al., "Gene-expression profiles to predict distant metastasis of lymph-node-negative primary breast cancer". Lancet 19-25;365(9460):671-9, 2005.

Ward and Moul, "Rising prostate-specific antigen after primary prostate cancer therapy", *Nat Clin. Pract. Urol.*, 2(4):174-182, 2005.

Wright et al., "Differences in prostate cancer outcomes between cases with Gleason 4+3 and Gleason 3+4 tumors in a population-based cohort", *J. Urol.*, 182(6):2702-2707, 2009.

Wu et al., "Glucocorticoid receptor activation signals through forkhead transcription factor 3a in breast cancer cells" Mol. Endocrinol, 20(10): 2304-14, 2006.

Wu et al., "Microarray analysis reveals glucocorticoid-regulated survival genes that are associated with inhibition of apoptosis in breast epithelial cells" Cancer Res., 64(5):1757-64, 2004.

Wu et al., "Prevalent expression of the immunostimulatory MHC class I chain-related molecule is counteracted by shedding in prostate cancer" J. Clin. Invest., 114(4):560-8, 2004.

Xie et al., "The expression of glucocorticoid receptor is negatively regulated by active androgen receptor signaling in prostate tumors", *Int. J. Cancer*, 136:E27-E38, 2015.

Yemelyanov et al., "Tumor suppressor activity of glucocorticoid receptor in the prostate", *Oncogene*, 26(13):1885-1896, 2007.

Zegarra-Moro et al., "Disruption of Androgen Receptor Function Inhibits Proliferation of Androgen-refractory Prostate Cancer Cells", *Cancer Res.*, 62(4):1008-1013, 2002.

Zhao et al., "Glucocorticoid Receptor in Prostate Epithelia is not Required for Corticosteroid-Induced Epithelial Hyperproliferation in the Mouse Prostate", *The Prostate*, 74:1068-1078, 2014.

Zou et al., "Androgen-Induced Coactivator ANCCA Mediates Specific Androgen Receptor Signaling in Prostate Cancer", *Cancer Res.*, 69(8):3339-3346, 2009.

* cited by examiner

METHODS AND COMPOSITIONS RELATED TO HSP90 INHIBITORS AND BREAST CANCER

CROSS-REFERENCE TO RELATED APPLICATIONS

This application is a national phase application under 35 U.S.C. § 371 of International Application No. PCT/US2014/070032 filed on Dec. 12, 2014, which claims priority to U.S. Provisional Application No. 61/915,411 filed on Dec. 12, 2013. The entire contents of each of the above-referenced disclosures are specifically incorporated herein by reference without disclaimer.

STATEMENT OF GOVERNMENT RIGHTS

This invention was made with government support under CA149472 awarded by the National Institutes of Health. The government has certain rights in the invention.

BACKGROUND OF THE INVENTION

I. Field of the Invention

Embodiments are directed generally to biology and medicine. In certain aspects there are methods and compositions for treating a cancer patient, particularly a breast cancer patient, with an Hsp90 inhibitor with or without chemotherapy. In other embodiments, there are methods and compositions for evaluating a patient with triple-negative breast cancer based on expression of glucocorticoid receptor and/or androgen receptor.

II. Background

There are over 1 million cases of breast cancer per year on a global basis, of which around 0.5 million are in the US, 40,000 are in the UK and nearly 2,000 in Ireland. It is the leading cause of cancer deaths among women (Keen and Davidson, 2003). Although the overall incidence of the disease is increasing within the western world, wider screening and improved treatments have led to a gradual decline in the fatality rate of about 1% per year since 1991. Inheritance of susceptibility genes, such as BRCA1 and BRCA2, account for only 5% of breast cancer cases and the factors responsible for the other 95% remain obscure (Grover and Martin, 2002).

Hsp90 inhibitors with increased potency and reduced toxicity are being revisited as a treatment for TNBC. Despite recent advances, the challenge of cancer treatment, including breast cancer therapy remains. Progress is limited with respect to the development of specific treatment regimens to clinically distinct tumor types, and to personalize tumor treatment in order to maximize outcome and efficiency. Moreover, a number of patients exhibit chemotherapy resistance.

Mere classification of breast cancers into a few subgroups characterized by low to absent gene expression of the estrogen receptor (ER) alone may not reflect the cellular and molecular heterogeneity of breast cancer, and may not allow the design of treatment strategies maximizing patient response. Once a patient is diagnosed with cancer, such as breast or ovarian cancer, or an individual wants predisposition analysis, there is a strong need for methods that allow the physician to predict the expected course of disease, including the likelihood of cancer recurrence, long-term survival of the patient, and the like, and accordingly select an appropriate treatment option that is effective.

SUMMARY OF THE INVENTION

Embodiments concern methods, compositions, and apparatuses related to assessing, prognosing, and/or treating breast cancer patients. In particular, it relates to identifying patients who are most likely to benefit from a particular treatment with Hsp90 inhibitors. In some embodiments, it concerns using information related to glucocorticoid receptor (GR) activity and/or expression in conjunction with information related to androgen receptor (ER) activity or expression to identify patients who may respond to a combination treatment that involves an Hsp90 inhibitor and chemotherapy. Such a patient may be one who has breast cancer that is susceptible to becoming or is chemoresistant.

Accordingly, methods concern treating and/or evaluating a patient with a cancer such as breast cancer. In certain aspects, the cancer to be treated, evaluated or diagnosed may be brain, lung, liver, spleen, kidney, lymph node, small intestine, pancreas, blood cells, colon, stomach, breast, endometrium, prostate, testicle, ovary, skin, head and neck, esophagus, bone marrow or blood cancer. Particularly, it may be breast cancer, ovarian cancer, or prostate cancer, such as castrate-resistant cancer. All of the embodiments that apply to breast cancer, breast cancer cells, or breast cancer patients may apply to other cancer, other types of cancer cells, or other types of cancer patients as well.

Embodiments include evaluating a biological sample from a patient; evaluating breast cancer cells from a patient; evaluating a biological sample from a breast cancer patient; assessing a breast cancer patient; testing a breast cancer sample or biopsy; testing a breast tumor; treating a breast cancer patient, particularly a patient with a particular profile related to one or more of GR, AR, ER, PR, and/or Her2/neu (triple-negative status—see Lehmann, 2011 for triple-negative definition, which is hereby incorporated by reference); determining a treatment for a breast cancer patient; altering a treatment plan for a breast cancer patient; generating an expression profile for a breast cancer patient involving one or more of GR, AR, ER, PR, and/or Her2/neu; comparing a patient's GR and/or AR expression profile to a standardized profile; and/or, evaluating and/or determining treatment options for a breast cancer patient based on the patient's AR and/or GR status (alone or in combination with triple-negative status). In additional embodiments, methods may involve obtaining or evaluating circulating tumor cells.

Some embodiments include methods of treating breast cancer comprising administering to a patient an effective amount of a combination of anti-cancer compounds, wherein the anticancer compounds comprise an Hsp90 inhibitor and a chemotherapeutic, and wherein the patient has breast cancer cells that are chemo-resistant or not chemo-sensitive. In some embodiments, the patient has been determined to have breast cancer cells that are chemo-resistant or not chemo-sensitive. In some embodiments, the patient has breast cancer cells that do not express detectable levels of any of estrogen receptor, progesterone receptor, and Her2/neu. In some embodiments, the patient has been determined to have breast cancer cells that do not express detectable levels of any of estrogen receptor, progesterone receptor, and Her2/neu. In some embodiments, the patient has breast cancer cells that are glucocorticoid receptor positive (GO. In some embodiments, the patient is suspected of having breast cancer cells that are $GR^+$. In some embodiments, the patient has been determined to have breast cancer cells that are $GR^+$. In some embodiments, the patient has breast cancer cells that are androgen receptor positive ($AR^+$). In some embodiments, the patient is suspected of having breast cancer cells that are AR+. In some embodiments, the patient has been determined to have breast cancer cells that are androgen receptor positive (AR+). In some embodiments, the patient was previously administered a first chemotherapeutic more than two weeks prior to the combination of anti-cancer compounds. In some embodiments, each of the anti-cancer compounds is administered within one week of the other. In some embodiments, each of the anti-cancer compounds is administered within 24 hours of the other. In some embodiments, In some embodiments, the Hsp90 inhibitor is administered prior to the chemotherapeutic. In some embodiments, the Hsp90 inhibitor is administered up to three days prior to administering the chemotherapeutic. In some embodiments, the Hsp90 inhibitor is also administered after the chemotherapeutic. In some embodiments, the Hsp90 inhibitor is administered after the chemotherapeutic is administered. In some embodiments, the breast cancer is an unresectable breast cancer.

Some embodiments include methods of treating breast cancer comprising administering to a patient an effective amount of a combination of anti-cancer compounds, wherein the anticancer compounds comprise an Hsp90 inhibitor and a chemotherapeutic, and wherein the patient has breast cancer cells that are GR In some embodiments, the patient is suspected of having breast cancer cells that are GR+. In some embodiments, the patient has been determined to have breast cancer cells that are GR+. In some embodiments, the patient is suspected of having breast cancer cells that are chemo-resistant or not chemo-sensitive. In some embodiments, the patient has been determined to have breast cancer cells that are chemo-resistant or not chemo-sensitive. In some embodiments, the patient has breast cancer cells that do not express detectable levels of any of estrogen receptor, progesterone receptor, and Her2/neu. In some embodiments, the patient has been determined to have breast cancer cells that do not express detectable levels of any of estrogen receptor, progesterone receptor, and Her2/neu. In some embodiments, the patient has breast cancer cells that are androgen receptor positive (AR+). In some embodiments, the patient is suspected of having breast cancer cells that are AR+. In some embodiments, the patient has been determined to have breast cancer cells that are androgen receptor positive (AR+). In some embodiments, the patient was previously administered a first chemotherapeutic more than two weeks prior to the combination of anti-cancer compounds. In some embodiments, each of the anti-cancer compounds is administered within one week of the other. In some embodiments, each of the anti-cancer compounds is administered within 24 hours of the other. In some embodiments, the Hsp90 inhibitor is administered prior to the chemotherapeutic. In some embodiments, the Hsp90 inhibitor is administered up to three days prior to administering the chemotherapeutic. In some embodiments, the Hsp90 inhibitor as also administered after the chemotherapeutic. In some embodiments, the Hsp90 inhibitor is administered after the chemotherapeutic is administered. In some embodiments, the breast cancer is an unresectable breast cancer.

Some embodiments include methods of treating breast cancer comprising administering to a patient an effective amount of a combination of a Hsp90 inhibitor followed by at least one apoptosis-inducing agent, wherein the patient has been determined to have breast cancer cells that are GR+. In some embodiments, the patient has been determined to have breast cancer cells that do not express detectable levels of any of estrogen receptor, progesterone receptor, and Her2/neu. In some embodiments, at least one apoptosis-inducing agent is radiation, a chemotherapeutic, or an immunotherapy. In some embodiments, the patient was previously administered a first apoptosis inducing agent more than two weeks prior to the Hsp90 inhibitor. In some embodiments, the patient has breast cancer cells that were resistant to apoptosis at the time of administration of the first apoptosis inducing agent. In some embodiments, the patient is determined to have breast cancer cells that are resistant to apoptosis. In some embodiments, the apoptosis-inducing agent is administered within 1 week of the Hsp90 inhibitor. In some embodiments, the Hsp90 inhibitor is administered up to three days prior to administering the apoptosis-inducing agent. In some embodiments, the breast cancer is an unresectable breast cancer.

Some embodiments include methods for treating breast cancer in a patient comprising: (a) administering radiation or at least a first chemotherapeutic to the patient; (b) subsequently administering an effective amount of a Hsp90 inhibitor to the patient; (c) administering radiation again or at least a second chemotherapeutic to the patient after the Hsp90 inhibitor is administered to the patient; wherein the patient is determined to have breast cancer cells that are GR+ or AR+.

Some embodiments include methods for treating breast cancer in a patient comprising: (a) administering an effective amount of a Hsp90 inhibitor to the patient, wherein the patient is determined to have breast cancer cells that express a detectable level of GR prior to administration of the Hsp90 inhibitor; (b) then administering an effective amount of radiation or at least one chemotherapeutic. In some embodiments, the breast cancer cells undergo apoptosis.

Some embodiments include methods of treating a patient for breast cancer comprising administering to the patient a therapy for breast cancer after a biological sample from the patient containing breast cancer cells is evaluated for the activity level of GR, wherein the patient is administered a therapy that is not an Hsp90 inhibitor if it is determined that the breast cancer cells do not have detectable GR activity, and wherein the patient is administered a therapy different from what would have been administered if the activity level of GR had not been evaluated. In some embodiments, the patient is treated with a therapy comprising an anti-angiogenic agent. In some embodiments, the therapy further comprises a chemotherapeutic agent in addition to the anti-angiogenic agent. In some embodiments, the therapy comprises a kinase inhibitor. In some embodiments, the therapy comprises radiation.

Embodiments also cover apparatuses, kits, and computer readable medium and systems for assessing the level or activity of AR and/or GR in a patient's breast cancer sample and determining a prognosis; and/or treating the patient accordingly. It is specifically contemplated that a breast cancer patient is a human. Accordingly, in human patients, AR refers to an androgen receptor in a human and GR refers to a glucocorticoid receptor in a human.

Some embodiments include generating an expression profile for glucocorticoid receptor, which means obtaining the level of expression of GR directly or indirectly by measuring or assaying activity or expression. Methods include directly measuring or assaying the level of expression or activity refers to measuring or assaying a sample to determine the level of GR expression (protein or transcript) in the cell. Indirectly obtaining the level of expression includes measuring or assaying expression or activity of a gene or protein that correlates with GR expression or activity. In some embodiments, the level of GR expression can be indirectly obtained by measuring or assaying expression of a GR-responsive gene, which refers to a gene whose expression is affected in a dose-dependent manner by GR expression or activity. Expression refers to either protein expression or RNA (transcript) expression. Methods may involve either type of expression and a variety of assays are well known to those of skill in the art. For example, quantitative PCR may be performed to obtain RNA expression levels. An Affymetrix chip also provides information regarding RNA expression levels. Alternatively, reagents to detect protein expression levels may be employed in embodiments. Methods may involve probes, primers, and/or antibodies that are specific to GR or AR in order to assess expression levels.

In some embodiments, the activity level of GR is measured by assaying the level of GR expression. In additional embodiments, GR expression is GR transcript expression. In other embodiments, GR expression is GR protein expression. As discussed above, in some embodiments, the activity level of GR is measured by assaying the expression level of one or more GR-responsive genes. A GR-responsive gene may include, but not be limited to, one or more of the following: MCL1, SAP30, SMARCA2, PTGDS, TNFRSF9, SFN, LAPTM5, GPSM2, SORT1, DPT, NRP1, ACSL5, BIRC3, NNMT, IGFBP6, PLXNC1, SLC46A3, C14orf139, PIAS1, IDH2, SERPINF1, ERBB2, PECAM1, LBH, ST3GAL5, IL1R1, BIN1, WIPF1, TFPI, FN1, FAM134A, NRIP1, RAC2, SPP1, PHF15, BTN3A2, SESN1, MAP3K5, DPYSL2, SEMA4D, STOM, MAOA, ANGPTL4 (Angiopoietin-like 4), BCL6 (B-cell CLL/lymphoma 6), CALCR (CALCITONIN RECEPTOR), CEBPB (CCAAT/enhancer binding protein (C/EBP), beta), DDIT4 (DNA-damage-inducible transcript 4), DUSP1 (Dual specificity phosphatase 1), EDN1 (Endothelin 1, ERRFI1 (ERBB receptor feedback inhibitor 1), FKBP5 (FK506 binding protein 5), GLUL (Glutamate-ammonia ligase), IL6R (Interleukin 6 receptor), KLF13 (Kruppel-like factor 13), KLF9 (Kruppel-like factor 9), LOX (Lysyl oxidase), MT1E (Metallothionein 1E), MT2A (Metallothionein 2A), NFKBIA (Nuclear factor of kappa light polypeptide gene enhancer in B-cells inhibitor), alpha, PER1 (Period homolog 1 (*Drosophila*)), RHOB (Ras homolog gene family, member B), SESN1 (Sestrin 1), SGK1 (Serum/glucocorticoid regulated kinase 1), SLC19A2 (Solute carrier family 19 (thiamine transporter), member 2), SLC22A5 (Solute carrier family 22 (organic cation/carnitine transporter), member 5), TNFAIP3 (Tumor necrosis factor, alpha-induced protein 3), TSC22D3 (TSC22 domain family, member 3), USP2 (Ubiquitin specific peptidase 2), XDH (Xanthine dehydrogenase), or ZFP36 (Zinc finger protein 36, C3H type, homolog (mouse)).

In some embodiments, there is a step of assaying or measuring the activity level of glucocorticoid receptor (GR) in a biological sample from the patient containing breast cancer cells. As discussed above, the activity level of GR can be obtained directly or indirectly. It is specifically contemplated that levels of glucocorticoid activity or expression refers to activity or expression of GR α, GR β, or both. Unless specifically stated otherwise, the terms "glucocorticoid receptor" or "GR" refer to both forms. Embodiments discussed with respect to glucocorticoid receptor or GR may also be implemented solely with GRα or solely with GRβ.

Methods may also include obtaining a level of androgen receptor (AR) expression in breast cancer cells from the patient. The level can be obtained by obtaining the results of an assay that measured the level of AR expression. In some embodiments, the level is obtained by measuring or assaying the level of AR expression.

In some embodiments, the level of androgen receptor expression in breast cancer cells from patient is obtained by measuring the level of androgen receptor expression from the biological sample from the patient. In other embodiments, the level is obtained by receiving qualitative and/or quantitative data regarding the level.

In some embodiments, methods include identifying the patient as having or not having a risk factor for cancer recurrence based on the levels of AR and GR expression. Methods may involve categorizing the patient as $AR^+$ or $AR^-$ based on the level of androgen receptor expression and a predetermined threshold value for AR expression. The term "$AR^+$" refers to a classification of AR expression that indicates the patient expresses androgen receptor in cancer cells at or above a certain level. The term "$AR^-$" refers to a classification of AR expression that indicates the patient expresses androgen receptor at a relatively low level in cancer cells, meaning at or below a certain level. In certain embodiments, that certain level or a predetermined threshold value is at, below, or above 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percentile, or any range derivable therein.

Methods may involve measuring the activity level of glucocorticoid receptor in a biological sample from the patient containing breast cancer cells and measuring the expression level of androgen receptor in the biological sample.

In certain embodiments, the predetermined threshold value for AR expression identifies a patient as $AR^+$ if the patient's AR expression level is in the $10^{th}$ percentile or greater compared to a normalized sample or is detectable by any methods known in the art. This means the patient may be designated as having a level of AR expression that is at or above 10, 11, 12, 13, 14, 15, 16, 17, 18, 19, 20 21, 22, 23 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percentile, or any range derivable therein. It is contemplated that in some cases, a patient may be designated as $AR^+$ if the patient's AR expression level is at or above 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or any range derivable therein. The patient may also be referred to as having a normal or high AR expression level. The higher the percentile, the higher the relative expression level.

In embodiments, methods may also involve categorizing the patient's tumor as $GR^+$ or $GR^-$ based on a predetermined threshold value for GR activity. In some cases, a predetermined threshold value for GR activity is dependent on whether the tumor is categorized as $AR^+$ or $AR^-$. Embodiments may involve a predetermined threshold value for GR activity that identifies a patient's tumor as $GR^+$ if the patient is $AR^+$ and GR activity level is in the $65^{th}$ percentile or greater compared to a normalized sample. The tumor may be identified as $GR^+$ if the tumor's GR expression level is detectable by any methods known in the art. It is contemplated that in some cases, a tumor may be designated as $GR^+$ if the tumor's GR expression level is at or above 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or any range derivable therein. The threshold value may or may not be dependent on AR expression levels or status. In some embodiments, the threshold value depends on whether the tumor is $AR^+$ or not. The higher the percentile, the higher the relative expression level.

Methods may involve the use of a normalized sample or control that is based on one or more breast cancer samples that are not from the patient being tested.

Other embodiments include methods of treating a patient for breast cancer comprising: treating the patient for breast cancer after a biological sample from the patient containing breast cancer cells is analyzed for i) the activity level of glucocorticoid receptor and ii) the expression level of androgen receptor. A patient may be treated with a different treatment protocol than the patient would have been treated with if the patient's biological sample had not been analyzed. In some embodiments, the patient is categorized as $AR^+$ and/or $GR^+$ based on the activity/expression level of the glucocorticoid receptor and the activity/expression level of androgen receptor. In some cases, the patient is treated with Hsp90 inhibitor with or without chemotherapy after being determined to be $AR^+$ and/or $GR^+$. In other cases, the patient is treated with a cancer therapy that is not Hsp90 inhibitor after being evaluated for GR and/or AR expression. In certain cases, the patient is treated with a cancer therapy that is not Hsp90 after the patient is determined to lack detectable levels of GR and/or AR expression in the patient's breast cancer cells. In some embodiments, the patient is treated with a therapy comprising an anti-angiogenic agent. In additional embodiments, the therapy further comprises a chemotherapeutic agent in addition to the anti-angiogenic agent.

Embodiments may also include methods where the patient is treated with more than one type of cancer therapy. This may be after the patient's tumor is determined to have a particular GR and AR expression profile. In some embodiments, certain treatments such as Hsp90 inhibitor and/or one or more chemotherapeutic agents are provided to an $AR^+$ and/or $GR^+$ breast cancer patient who might have otherwise been treated with a different cancer therapy. In some embodiments, a patient is treated with at least two of the following: radiation, chemotherapy, or a biologic. In further embodiments, the patient has been previously treated with chemotherapy but with limited success or the patient is determined to have chemoresistant breast cancer cells.

Methods may also involve obtaining a biological sample comprising breast cancer cells from the patient and categorizing the patient's tumor as i) $GR^+$ or $GR^-$ based on the level of glucocorticoid activity assayed in the sample and compared to a predetermined threshold value for GR activity; and ii) $AR^+$ or $AR^-$ based on the level of androgen receptor expression assayed in the sample and compared to a predetermined threshold value for AR expression.

Any method may also include treating the patient for breast cancer, which may include directly administering or providing a cancer therapy. In some embodiments, a practitioner or doctor may prescribe a cancer therapy that the patient administers to herself or himself.

To achieve these methods, a doctor, medical practitioner, or their staff may retrieve a biological sample from a patient for evaluation. The sample may be a biopsy, such as a breast tissue or tumor biopsy. The sample may be analyzed by the practitioner or their staff, or it may be sent to an outside or independent laboratory. The medical practitioner may be cognizant of whether the test is providing information regarding the patient's level of tumor GR and/or AR expression or activity, or the medical practitioner may be aware only that the test indicates directly or indirectly that the test reflects that the patient has a particular prognosis or can be given a particular prognosis score. Furthermore, the practitioner may know the patient's tumor AR or GR status, such as $AR^+$ or $AR^-$, or $GR^+$ or $GR^-$. Alternatively, she or he may be aware only that the test or assay indicates the patient has a poor prognosis, or the worst prognosis.

Embodiments also concern kits to determine glucocorticoid receptor status in cancer cells, especially breast cancer cells, comprising: (a) one or more reagents for determining expression levels of glucocorticoid receptor gene NR3C1 in a biological sample; and (b) an algorithm and software encoding the algorithm for calculating a risk factor index from the expression of NR3C1 in a sample and the androgen receptor (AR) status of the breast cancer cells to determine a prognosis or a prognosis score. Kits may also include one or more reagents for determining expression levels of the androgen receptor (AR) gene (NM_000044) in the biological sample to provide androgen receptor (AR) status.

Other embodiments include a computer readable medium having software modules for performing a method comprising the acts of: (a) comparing glucocorticoid receptor data obtained from a patient's breast cancer sample with a reference; and (b) providing an assessment of glucocorticoid receptor status to a physician for use in determining an appropriate therapeutic regimen for a patient. In further embodiments, the computer readable medium further comprises a software module for assessing androgen receptor status of the patient's breast cancer sample. In further embodiments, the computer readable medium further comprises a software module for assessing triple negative status of the patient's breast cancer sample.

Computer systems are also included. In some embodiments, they have a processor, memory, external data storage, input/output mechanisms, a display, for assessing glucocorticoid receptor activity, comprising: (a) a database; (b) logic mechanisms in the computer generating for the database a GR-responsive gene expression reference; and (c) a comparing mechanism in the computer for comparing the GR-responsive gene expression reference to expression data from a patient sample using a comparison model to determine a GR gene expression profile of the sample.

Other embodiments include an internet accessible portal for providing biological information constructed and arranged to execute a computer-implemented method for providing: (a) a comparison of gene expression data of one or more GR-responsive genes in a patient sample with a calculated reporter index; and (b) providing an assessment of GR activity or expression to a physician for use in determining an appropriate therapeutic regime for a patient.

In addition to compiling, collecting and or processing data related to GR status, methods, media and systems may also include the same embodiments with respect to data related to AR status. Such aspects may be instead of or in addition to the aspects related to GR status or data.

Embodiments also include methods of killing breast cancer cells comprising administering to a breast cancer patient an effective amount of a combination of anti-cancer compounds, wherein the anticancer compounds comprise an Hsp90 inhibitor and a chemotherapeutic.

In other embodiments, there are methods for treating breast cancer in a patient comprising administering to the patient an effective amount of an Hsp90 inhibitor and a chemotherapeutic.

In further embodiments, methods are provided for treating chemotherapy-insensitive breast cancer cells comprising administering to a breast cancer patient an effective amount of an Hsp90 inhibitor followed by chemotherapy.

Other methods include methods for treating breast cancer in a patient comprising: a) administering radiation or at least a first chemotherapeutic to the patient; b) subsequently administering an effective amount of an Hsp90 inhibitor to the patient; and, c) administering radiation again or at least a second chemotherapeutic to the patient after the Hsp90 inhibitor is administered to the patient.

In some embodiments, there are methods for treating breast cancer in a patient comprising: a) administering an effective amount of an Hsp90 inhibitor to the patient, wherein the patient expresses detectable levels of GR prior to administration of the Hsp90 inhibitor; b) then administering an effective amount of radiation or at least one chemotherapeutic.

It is contemplated that in methods described herein, breast cancer cells may undergo apoptosis following treatment set forth herein. Moreover, in some embodiments, the combination of an Hsp90 inhibitor and an anticancer agent or compound induces more apoptosis than treatment with just the anticancer treatment alone. In other methods, it is specifically contemplated to exclude treatment with a synthetic glucocorticoid, such as dexamethasone.

Hsp90 inhibitors are known to those of skill in the art. It is defined as a compound or substance that inhibits the activity of an Hsp90 protein. In some embodiments, the Hsp90 inhibitors are Hsp90 inhibitors that have been determined to inhibit the activity of an Hsp90 protein. In additional embodiments, the Hsp90 inhibitors are non-naturally occurring compounds or substance, such as chemically synthesized compounds or substance.

Examples of Hsp90 inhibitors include, but are not limited to, geldanamycin, ganetespib, radicicol, 17-N-Allylamino-17-demethoxygeldanamycin/tanespicmycin/17AAG (BMS), 17-DMAG, herbimycin A, novobiocin sodium (U-6591), 17-GMB-APA-GA, macbecin I, CCT 018159, gedunin, PU24FC1, PU-H71, PU-DZ8, PU3, AUY922 (Novartis), HSP990 (Novartis), retaspimycin hydrochloride/IPI-504 (Infinity), BIIB021/CNF2024 (Biogen Idec), STA-9090 (Synta), IPI-493 (Infinity), SNX-5422/mesylate (Pfizer), BIIB028 (Biogen Idec), KW-2478 (Kyowa Hakko Kirin), AT13387 (Astex), XL888 (Exelixis), MPC-3100 (Myriad), ABI-010/nab (nanoparticle, albumin bound)-17AAG (Abraxis). It is specifically contemplated that one or more of the Hsp90 discussed herein, in the incorporated references, or known to those of skill in the art may be excluded in certain embodiments. In certain embodiments, Hsp90 inhibitors used herein may not be a GR antagonist or may not bind to GR, even though they may downregulate GR expression. For example, Hsp90 inhibitors used herein may not block or antagonize GR activation, reverse GR-mediated cell survival signaling, or reverse GR-mediated cell survival.

In some embodiments, a patient had previously been treated with an anti-cancer therapy, such as radiation, chemotherapy, or immunotherapy (or a combination or multiple therapies thereof). In certain embodiments, a first anti-cancer therapy prior to therapy with an Hsp90 inhibitor was last administered more than two weeks prior to the Hsp90 inhibitor or its combination with a second anti-cancer therapy. In certain embodiments, this first anti-cancer therapy that does not include a Hsp90 inhibitor was last administered to the breast cancer patient at least 7, 8, 9, 10, 11, 12, 13, 14 days, and/or 1, 2, 3, 4, or 5 weeks, and/or 1, 2, 3, 4, 5, 6, 7, 8, 9, 10, 11, or 12 months (or any range derivable therein) prior to treatment with a Hsp90 inhibitor. Treatment methods may be applied to breast cancer or breast cancer cells that are chemo-resistant or breast cancer cells that are not chemo-sensitive. Moreover, treatment may be applied to breast cancer or to breast cancer cells that were previously administered a first apoptosis inducing agent, but were resistant to apoptosis.

In some embodiments, the breast cancer cells are determined to be resistant to apoptosis. In additional embodiments, the breast cancer or the breast cancer cells are determined not to be chemo-sensitive or are determined to be chemo-resistant. This determination may be based on the results of a genetic test or based on information obtained from an assessment of a tumor or the breast cancer after treatment with a first anti-cancer therapy. In specific embodiments, the first anti-cancer therapy is a chemotherapeutic, Herceptin®, radiation, a combination of chemotherapeutics, or a combination of one or more chemotherapeutic agents and Herceptin®.

In additional embodiments, the breast cancer cells express a detectable level of glucocorticoid receptor or its transcript. In some embodiments, the patient is determined to have breast cancer cells that express a detectable level of glucocorticoid receptor or its transcript. This may be determined directly or indirectly.

It is contemplated that breast cancer cells may be treated with an Hsp90 inhibitor regardless of androgen receptor status. Therefore, breast cancer cells may be androgen receptor-positive ($AR^+$) or androgen receptor-negative ($AR^-$), accordingly to a standardized and industry accepted test for AR status. In certain embodiments, the breast cancer cells express detectable levels of AR; in other embodiments, AR expression is detectable in the breast cancer cells. In certain other embodiments, the level of AR expression is at or below the normal or normalized level of AR expression for triple negative breast cancer.

Methods involve treating breast cancer, including but not limited to a chemo-resistant breast cancer, with a combination of therapies that includes an Hsp90 inhibitor and an anticancer therapy that induces apoptosis (together they may be referred to as a combination of anti-cancer agents or compounds), such as a chemotherapeutic. In some embodiments, the chemotherapeutic is capecitabine, carboplatin, cyclophosphamide (Cytoxan), daunorubicin, docetaxel (Taxotere), doxorubicin (Adriamycin), epirubicin (Ellence), fluorouracil (also called 5-fluorouracil or 5-FU), gemcitabine, eribulin, ixabepilone, methotrexate, mitomycin C, mitoxantrone, paclitaxel (Taxol), thiotepa, vincristine, or vinorelbin, or a combination of these agents. In other embodiments, therapy with a Hsp90 inhibitor is combined Herceptin®, radiation, chemotherapeutic(s) and radiation, a combination of chemotherapeutics, or a combination of one or more chemotherapeutic agents and Herceptin®.

It is contemplated that in some embodiments of the combination therapy the Hsp90 inhibitor is administered within 5, 10, 30, 45, 60 minutes, and/or 1, 2, 3, 4, 5, 6, 7, 8, 9, 10, 11, 12, 13, 14, 15, 16, 17, 18, 19, 20, 21, 22, 23, 24 hours, and/or 1, 2, 3, 4, 5, 6, 7 days, or any combination thereof within administration of at least one or the combination of the anti-cancer agents or compounds. In specific embodiments, the Hsp90 inhibitor is administered within 2 hours, 12 hours or 24 hours of administration of an anticancer agent or compound (or a combination of such agents or compounds).

It is specifically contemplated that treatment may continue or be repeated. In some embodiments, once treated with the combination of an Hsp90 inhibitor and at least one anticancer agent or compound, all or part of the treatment may be repeated alone or in combination with a different anticancer agent or compound.

In certain embodiments, the Hsp90 inhibitor is administered prior to the other agent or therapy included in the combination therapy. In certain embodiments, the Hsp90 inhibitor is administered 5, 10, 30, 45, 60 minutes, and/or 1, 2, 3, 4, 5, 6, 7, 8, 9, 10, 11, 12, 13, 14, 15, 16, 17, 18, 19, 20, 21, 22, 23, 24 hours, and/or 1, 2, 3, 4, 5, 6, 7 days, or any combination thereof prior to administration of at least one or the combination of the anti-cancer agents or compounds. It is specifically contemplated that in some embodiments, the Hsp90 inhibitor is given prior to administration of the anticancer agent or compound but that the Hsp90 inhibitor is also given concurrently with or after administration of the initial or a subsequent dose of the anticancer agent or compound. As discussed throughout, the anticancer agent or compound may be in a combination of such agents or compounds. In certain embodiments, the Hsp90 inhibitor is administered up to three days prior to administering the anticancer agent or compound.

Additionally or alternatively, the Hsp90 inhibitor is administered after administration of the other agent or therapy included in the combination therapy. In certain embodiments, the Hsp90 inhibitor is administered 5, 10, 30, 45, 60 minutes, and/or 1, 2, 3, 4, 5, 6, 7, 8, 9, 10, 11, 12, 13, 14, 15, 16, 17, 18, 19, 20, 21, 22, 23, 24 hours, and/or 1, 2, 3, 4, 5, 6, 7 days, or any combination thereof after administration of at least one or the combination of the anti-cancer agents or compounds. It is specifically contemplated that in some embodiments, the Hsp90 inhibitor is given after administration of the anticancer agent or compound; such administration may be repeated. As discussed throughout, the anticancer agent or compound may be in a combination of such agents or compounds. In certain embodiments, the Hsp90 inhibitor is administered up to three days after administering the anticancer agent or compound.

In certain embodiments, the breast cancer is an unresectable breast cancer. In further embodiments, the breast cancer is inflammatory breast cancer.

Compositions are contemplated to include a Hsp90 inhibitor and any other anticancer compound discussed herein, such a Herceptin or one or more chemotherapeutic compounds. In some embodiments, the composition is in a pharmaceutically acceptable formulation.

Use of the one or more compositions may be employed based on methods described herein. Other embodiments are discussed throughout this application. Any embodiment discussed with respect to one aspect of the invention applies to other aspects of the invention as well and vice versa. The embodiments in the Example section are understood to be embodiments o that are applicable to all aspects of the technology described herein.

The term "recurrence" refers to the detection of breast cancer in the form of metastatic spread of tumor cells, local recurrence, contralateral recurrence or recurrence of breast cancer at any site of the body of the patient after breast cancer had been substantially undetectable or responsive to treatments.

By "gene" is meant any polynucleotide sequence or portion thereof with a functional role in encoding or transcribing a protein or regulating other gene expression. The gene may consist of all the nucleic acids responsible for encoding a functional protein or only a portion of the nucleic acids responsible for encoding or expressing a protein. The polynucleotide sequence may contain a genetic abnormality within exons, introns, initiation or termination regions, promoter sequences, other regulatory sequences or unique adjacent regions to the gene.

As used herein, "treatment" or "therapy" is an approach for obtaining beneficial or desired clinical results. This includes: reduce the number of cancer cells; reduce the tumor size; inhibit (i.e., slow to some extent and/or stop) cancer cell infiltration into peripheral organs; inhibit (i.e., slow to some extent and/or stop) tumor metastasis; inhibit, to some extent, tumor growth; and/or relieve to some extent one or more of the symptoms associated with the disorder, shrinking the size of the tumor, decreasing symptoms resulting from the disease, increasing the quality of life of those suffering from the disease, decreasing the dose of other medications required to treat the disease, delaying the progression of the disease, and/or prolonging survival of patients.

The term "therapeutically effective amount" refers to an amount of the drug that may reduce the number of cancer cells; reduce the tumor size; inhibit (i.e., slow to some extent and particularly stop) cancer cell infiltration into peripheral organs; inhibit (i.e., slow to some extent and particularly stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

The terms "overexpress", "overexpression", "overexpressed", "up-regulate", or "up-regulated" interchangeably refer to a biomarker that is transcribed or translated at a detectably greater level, usually in a cancer cell, in comparison to a non-cancer cell or cancer cell that is not associated with the worst or poorest prognosis. The term includes overexpression due to transcription, post transcriptional processing, translation, post-translational processing, cellular localization, and/or RNA and protein stability, as compared to a non-cancer cell or cancer cell that is not associated with the worst or poorest prognosis. Overexpression can be detected using conventional techniques for detecting mRNA (i.e., RT-PCR, PCR, hybridization) or proteins (i.e., ELISA, immunohistochemical techniques, mass spectroscopy). Overexpression can be 10%, 20%, 30%, 40%, 50%, 60%, 70%, 80%, 90% or more (or any range derivable therein) in comparison to a normal cell or cancer cell that is not associated with the worst or poorest prognosis. In certain instances, overexpression is 1-fold, 2-fold, 3-fold, 4-fold 5, 6, 7, 8, 9, 10, or 15-fold or more higher levels (or any range derivable therein) of transcription or translation in comparison to a non-cancer cell or cancer cell that is not associated with the worst or poorest prognosis. The comparison may be a direct comparison where the expression level of a control is measured at the same time as the test sample or it may be a level of expression that is determined from a previously evaluated sample or an average of levels of expression of previously evaluated sample(s).

"Biological sample" includes sections of tissues such as biopsy and autopsy samples, and frozen sections taken for histologic purposes. Such samples include breast cancer tissues, cultured cells, e.g., primary cultures, explants, and transformed cells. A biological sample is typically obtained from a mammal, such as a primate, e.g., human.

A "biopsy" refers to the process of removing a tissue sample for diagnostic or prognostic evaluation, and to the tissue specimen itself. Any biopsy technique known in the art can be applied to the diagnostic and prognostic methods. The biopsy technique applied will depend on the tissue type to be evaluated (e.g., breast), the size and type of the tumor, among other factors. Representative biopsy techniques include, but are not limited to, excisional biopsy, incisional biopsy, needle biopsy, and surgical biopsy. An "excisional biopsy" refers to the removal of an entire tumor mass with a small margin of normal tissue surrounding it. An "incisional biopsy" refers to the removal of a wedge of tissue that includes a cross-sectional diameter of the tumor. A diagnosis or prognosis made by endoscopy or fluoroscopy can require a "core-needle biopsy", or a "fine-needle aspiration biopsy" which generally obtains a suspension of cells from within a target tissue. Biopsy techniques are discussed, for example, in Harrison's Principles of Internal Medicine, 2005. Obtaining a biopsy includes both direct and indirect methods, including obtaining the biopsy from the patient or obtaining the biopsy sample after it is removed from the patient.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 5C. Androgen (R1881, 1 nM) pre-treatment for 2 hours also induced expression of the AR target gene TMPRSS2 which was decreased by concomitant ganetespib (50 nM) treatment.

FIG. 7A. Ganetespib (150 nM) and paclitaxel (10 nM) is not synergistic in GR-depleted MDA-MB-231 cells demonstrating the requirement for GR. Cells death was analyzed by the mitochondrial membrane potential assay. FIG. 7B. Doxycycline (dox)-inducible GR-depleted MDA-MB-231 cells (clone #1=GRD#1 and clone 3) and MDA-MB-231 GR-intact non silencing control (NSC) were established for the experiments in FIG. 7A.

FIG. 8A. GR$^+$ MDA-MB-231 xenograft study showing efficacy of paclitaxel (pac, 10 mg/kg) and ganetespib (gan, 150 mg/kg) compared to either agent alone. FIG. 8B. GR protein levels in the same tumors treated in FIG. 8A.

DETAILED DESCRIPTION OF THE INVENTION

Hsp90 inhibitors in clinical trials (ganetespib and NVP-AUY922) competitively bind to the amino-terminal ATP binding pocket of Hsp90 and inhibit ATPase activity. This causes oncogenic proteins to misfold and to be degraded by the proteasome. Hsp90 inhibitors can potentiate the effects of taxane chemotherapy in many cancers including TNBC.

Figure 1:
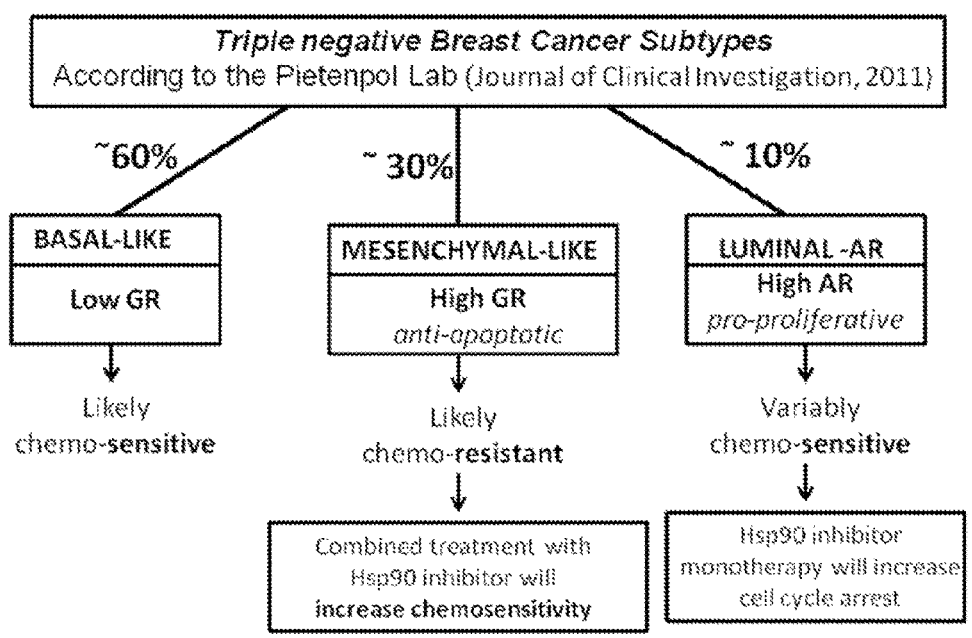
FIG. 1. Triple-negative breast cancer subtypes and chemotherapy sensitivity
Figure 2:
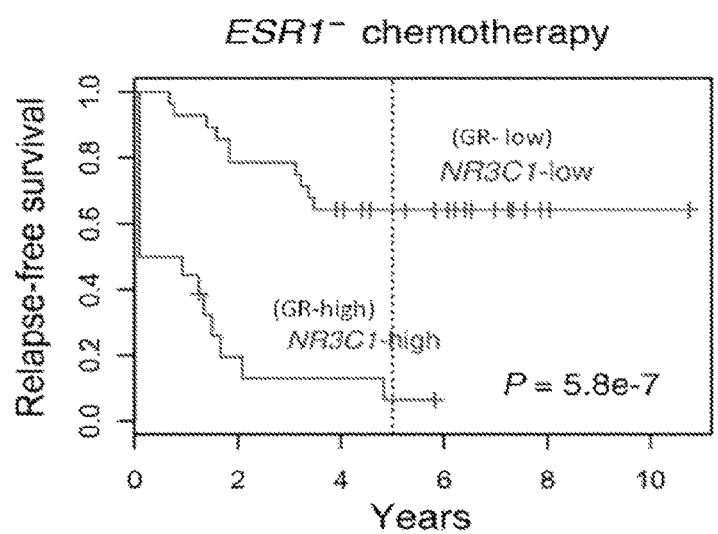
FIG. 2. High tumor GR (NR3C1) transcript expression in early-stage ER-breast cancer is associated with higher relapse rates FIG. 3. Hsp90 plays a crucial role in nuclear receptor activation and Hsp90 inhibition can potentially inhibit adverse anti-apoptotic (GR-mediated) and pro-proliferative (AR-mediated) signaling FIGS. 4A-4B.
Figure 3:
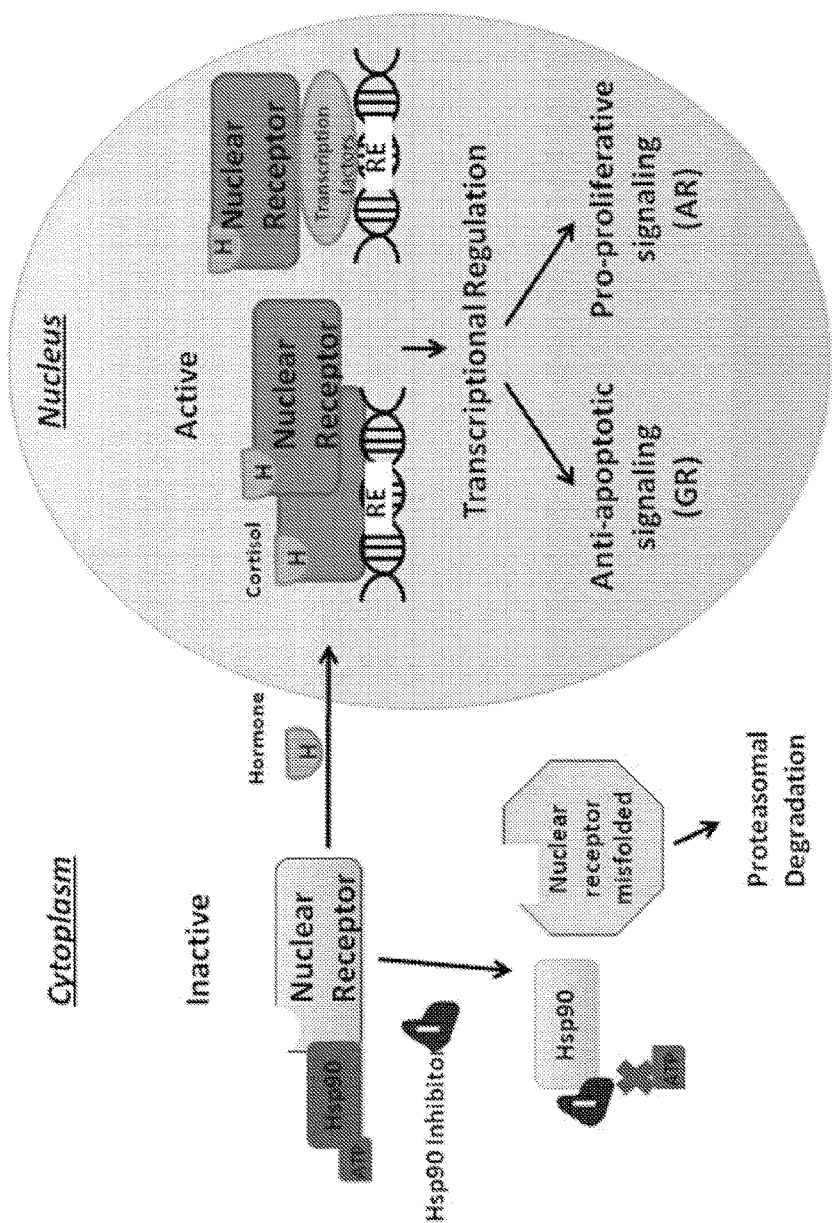

Depletion of GR and AR protein, following Hsp90 inhibition, are expected to simultaneously diminish the expression of anti-apoptotic (GR) and pro-proliferative (AR) target genes (FIGS. 1-2).

The experiments described in the Examples below show the following: 1) Hsp90 inhibitor treatment of TNBC cells results in proteasome-mediated degradation of GR and AR; 2) GR and AR transcriptional activity is decreased following Hsp90 inhibitor treatment; 3) addition of Hsp90 inhibitor to paclitaxel leads to increased cell death in vitro and in vivo; and, 4) GR expression is required for increased cell death following addition of an Hsp90 inhibitor to paclitaxel.

I. Hormone Receptor Status of Breast Cancer

Triple negative breast cancers (TNBC) have few common molecular drivers, therefore standard treatment is currently limited to chemotherapy. TNBCs are biologically heterogeneous and recent studies (Lehmann, B D et al., 2011, herein incorporated by reference), have classified them into subtypes which include: 1) basal-like, 2) mesenchymal-like and 3) luminal-AR (FIG. 1).

In estrogen receptor negative (ER−) premalignant and breast cancer epithelial cells, glucocorticoid receptor (GR) is a pro-survival transcription factor in the context of cytotoxic stressors such as chemotherapy (Moran, 2000; Pang, 2006). Activated GR up-regulates anti-apoptotic genes expression, e.g. SGK1 and MKP1.

In TNBC, androgen receptor (AR) activity is also pro-proliferative (Robinson, 2011; McNamara, 2013). A significant number of TNBC are, or become, chemotherapy-resistant. TNBCs with GR expression (approximately 30% of TNBCs) are associated with a worse prognosis (Pan, 2011, FIG. 2). AR is overexpressed in about 10% of TNBCs.

Biomarkers for prognosing human breast cancer patients have been identified. They include androgen receptor (AR) in combination with the activity of the glucocorticoid receptor (GR) activity. It is contemplated that these biomarkers may be evaluated based on their gene products. In some embodiments, the gene product is the RNA transcript. In other embodiments, the gene product is the protein expressed by the RNA transcript. In still another embodiment is the evaluation of surrogate genes or gene targets of AR, GR, or AR and GR.

In certain aspects a meta-analysis of expression or activity can be performed. In statistics, a meta-analysis combines the results of several studies that address a set of related research hypotheses. This is normally done by identification of a common measure of effect size, which is modeled using a form of meta-regression. Generally, three types of models can be distinguished in the literature on meta-analysis: simple regression, fixed effects meta-regression and random effects meta-regression. Resulting overall averages when controlling for study characteristics can be considered meta-effect sizes, which are more powerful estimates of the true effect size than those derived in a single study under a given single set of assumptions and conditions. A meta-gene expression value, in this context, is to be understood as being the median of the normalized expression of a marker gene or activity. Normalization of the expression of a marker gene may be particularly achieved by dividing the expression level of the individual marker gene to be normalized by the respective individual median expression of this marker genes, wherein said median expression is particularly calculated from multiple measurements of the respective gene in a sufficiently large cohort of test individuals. The test cohort particularly comprises at least 3, 10, 100, 200, 1000 individuals or more including all values and ranges thereof. Dataset-specific bias can be removed or minimized allowing multiple datasets to be combined for meta-analyses (See Sims et al. BMC Medical Genomics (1:42), 1-14, 2008, which is incorporated herein by reference in its entirety).

The calculation of a meta-gene expression value is performed by: (i) determining the gene expression value of at least two, particularly more genes (ii) "normalizing" the gene expression value of each individual gene by dividing the expression value with a coefficient which is approximately the median expression value of the respective gene in a representative breast cancer cohort (iii) calculating the median of the group of normalized gene expression values.

A gene shall be understood to be specifically expressed in a certain cell type if the expression level of said gene in said cell type is at least 2-fold, 5-fold, 10-fold, 100-fold, 1000-fold, or 10000-fold higher than in a reference cell type, or in a mixture of reference cell types. Reference cell types include non-cancerous breast tissue cells or a heterogeneous population of breast cancers.

In certain algorithms a suitable threshold level is first determined for a marker gene. The suitable threshold level can be determined from measurements of the marker gene expression in multiple individuals from a test cohort. The median expression of the marker gene in said multiple expression measurements is taken as the suitable threshold value.

Comparison of multiple marker genes with a threshold level can be performed as follows:

1. The individual marker genes are compared to their respective threshold levels.
2. The number of marker genes, the expression level of which is above their respective threshold level, is determined.
3. If a marker genes is expressed above its respective threshold level, then the expression level of the marker gene is taken to be "above the threshold level".

In certain aspects, the determination of expression levels is on a gene chip, such as an Affymetrix™ gene chip.

In another aspect, the determination of expression levels is done by kinetic real time PCR.

In certain aspects, the methods can relate to a system for performing such methods, the system comprising (a) apparatus or device for storing data on the AR or nodal status of the patient; (b) apparatus or device for determining the expression level of at least one marker gene or activity; (c) apparatus or device for comparing the expression level of the first marker gene or activity with a predetermined first threshold value; (d) apparatus or device for determining the expression level of at least one second marker gene or activity; and (e) computing apparatus or device programmed to provide a unfavorable or poor prognosis if the data indicates a negative AR status and an increased or decreased expression level of said first marker gene or activity (e.g., GR expression or activity) with the predetermined first threshold value and, alternatively, the expression level of said second marker gene is above or below a predetermined second threshold level.

The person skilled in the art readily appreciates that an unfavorable or poor prognosis can be given if the expression level of the first marker gene with the predetermined first threshold value indicates a tumor that is likely to recur or not respond well to standard therapies.

The expression patterns can also be compared by using one or more ratios between the expression levels of different breast cancer biomarkers. Other suitable measures or indicators can also be employed for assessing the relationship or difference between different expression patterns.

The GR nucleic acid and protein sequences are provided in GenBank accession number AY436590. The AR nucleic acid and protein sequences are provided in GenBank accession number (see above). The content of all of these GenBank Accession numbers is specifically incorporated herein by reference as of the filing date of this application.

The expression levels of breast cancer biomarkers can be compared to reference expression levels representing the same biomarker or a different marker using various methods. In certain aspects, the reference level may be a reference level of expression from a non-cancerous tissue from the same subject. Alternatively, the reference level may be a reference level of expression from a different subject or group of subjects. For example, the reference level of expression may be an expression level obtained from a sample (e.g., a tissue, fluid or cell sample) of a subject or group of subjects without cancer, or an expression level obtained from a non-cancerous tissue of a subject or group of subjects with cancer, breast cancer or other cancers. The reference level may be a single value or may be a range of values. The reference level of expression can be determined using any method known to those of ordinary skill in the art. In some embodiments, the reference level is an average level of expression determined from a cohort of subjects with cancer or without cancer. The reference level may also be depicted graphically as an area on a graph. In certain embodiments, a reference level is a normalized level, while in other embodiments, it may be a level that is not stable with respect to the tissue or biological sample being tested.

These reference levels can be determined using expression levels of a reference based on all breast cancer patients or all breast cancer patients determined to be $GR^+$, $GR^-$, $AR^+$ and/or $AR^-$. Alternatively, it can be based on an internal reference such as a gene that is expressed in all cells. In some embodiments, the reference is a gene expressed in breast cancer cells at a higher level than any biomarker. Any comparison can be performed using the fold change or the absolute difference between the expression levels to be compared. One or more breast cancer biomarkers may be used in the comparison. It is contemplated that 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 biomarkers (or any range derivable therein) may be compared to each other and/or to a reference that is internal or external. A person of ordinary skill in the art would know how to do such comparisons.

Comparisons or results from comparisons may reveal or be expressed as x-fold increase or decrease in expression relative to a standard or relative to another biomarker or relative to the same biomarker but in a different class of prognosis. In some embodiments, patients with a poor prognosis have a relatively high level of expression (overexpression) or relatively low level of expression (underexpression) when compared to patients with a better or favorable prognosis, or vice versa.

Fold increases or decreases may be, be at least, or be at most 1-, 2-, 3-, 4-, 5-, 6-, 7-, 8-, 9-, 10-, 11-, 12-, 13-, 14-, 15-, 16-, 17-, 18-, 19-, 20-, 25-, 30-, 35-, 40-, 45-, 50-, 55-, 60-, 65-, 70-, 75-, 80-, 85-, 90-, 95-, 100- or more, or any range derivable therein. Alternatively, differences in expression may be expressed as a percent decrease or increase, such as at least or at most 20, 25, 30, 35, 40, 45, 50, 55, 60, 65, 70, 75, 80, 85, 90, 95, 100, 110, 120, 130, 140, 150, 160, 170, 180, 190, 200, 300, 400, 500, 600, 700, 800, 900, 1000% difference, or any range derivable therein.

Other ways to express relative expression levels are by normalized or relative numbers such as 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, or any range derivable therein.

Algorithms, such as the weighted voting programs, can be used to facilitate the evaluation of biomarker levels. In addition, other clinical evidence can be combined with the biomarker-based test to reduce the risk of false evaluations. Other cytogenetic evaluations may be considered in some embodiments.

Any biological sample from the patient that contains breast cancer cells may be used to evaluate the expression pattern of any biomarker discussed herein. In some embodiments, a biological sample from a breast tumor is used. Evaluation of the sample may involve, though it need not involve, panning (enriching) for cancer cells or isolating the cancer cells.

A. Nucleic Acids

Screening methods based on differentially expressed gene products are well known in the art. In accordance with one aspect, the differential expression patterns of breast cancer biomarkers can be determined by measuring the levels of RNA transcripts of these genes, or genes whose expression is modulated by the these genes, in the patient's breast cancer cells. Suitable methods for this purpose include, but are not limited to, RT-PCR, Northern Blot, in situ hybridization, Southern Blot, slot-blotting, nuclease protection assay and oligonucleotide arrays.

In certain aspects, RNA isolated from breast cancer cells can be amplified to cDNA or cRNA before detection and/or quantitation. The isolated RNA can be either total RNA or mRNA. The RNA amplification can be specific or non-specific. Suitable amplification methods include, but are not limited to, reverse transcriptase PCR, isothermal amplification, ligase chain reaction, and Qbeta replicase. The amplified nucleic acid products can be detected and/or quantitated through hybridization to labeled probes. In some embodiments, detection may involve fluorescence resonance energy transfer (FRET) or some other kind of quantum dots.

Amplification primers or hybridization probes for a breast cancer biomarker can be prepared from the gene sequence or obtained through commercial sources, such as Affymatrix. In certain embodiments the gene sequence is identical or complementary to at least 8 contiguous nucleotides of the coding sequence.

Sequences suitable for making probes/primers for the detection of their corresponding cancer biomarkers include those that are identical or complementary to all or part of genes or SEQ ID NOs described herein. These sequences are all nucleic acid sequences of cancer biomarkers, including breast cancer biomarkers.

The use of a probe or primer of between 13 and 100 nucleotides, particularly between 17 and 100 nucleotides in length, or in some aspects up to 1-2 kilobases or more in length, allows the formation of a duplex molecule that is both stable and selective. Molecules having complementary sequences over contiguous stretches greater than 20 bases in length may be used increase stability and/or selectivity of the hybrid molecules obtained. One may design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

In one embodiment, each probe/primer comprises at least 15 nucleotides. For instance, each probe can comprise at least or at most 20, 25, 50, 75, 100, 125, 150, 175, 200, 225, 250, 275, 300, 325, 350, 400 or more nucleotides (or any range derivable therein). They may have these lengths and have a sequence that is identical or complementary to a gene or SEQ ID NO described herein. Particularly, each probe/primer has relatively high sequence complexity and does not have any ambiguous residue (undetermined "n" residues). The probes/primers particularly can hybridize to the target gene, including its RNA transcripts, under stringent or highly stringent conditions. In some embodiments, because each of the biomarkers has more than one human sequence, it is contemplated that probes and primers may be designed for use with each of these sequences. For example, inosine is a nucleotide frequently used in probes or primers to hybridize to more than one sequence. It is contemplated that probes or primers may have inosine or other design implementations that accommodate recognition of more than one human sequence for a particular biomarker.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

In another embodiment, the probes/primers for a gene are selected from regions which significantly diverge from the sequences of other genes. Such regions can be determined by checking the probe/primer sequences against a human genome sequence database, such as the Entrez database at the NCBI. One algorithm suitable for this purpose is the BLAST algorithm. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence to increase the cumulative alignment score. Cumulative scores are calculated using, for nucleotide sequences, the parameters M (reward score for a pair of matching residues; always >0) and N (penalty score for mismatching residues; always <0). The BLAST algorithm parameters W, T, and X determine the sensitivity and speed of the alignment. These parameters can be adjusted for different purposes, as appreciated by one of ordinary skill in the art.

In one embodiment, quantitative RT-PCR (such as TaqMan, ABI) is used for detecting and comparing the levels of RNA transcripts in breast cancer samples. Quantitative RT-PCR involves reverse transcription (RT) of RNA to cDNA followed by relative quantitative PCR (RT-PCR). The concentration of the target DNA in the linear portion of the PCR process is proportional to the starting concentration of the target before the PCR was begun. By determining the concentration of the PCR products of the target DNA in PCR reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived may be determined for the respective tissues or cells. This direct proportionality between the concentration of the PCR products and the relative mRNA abundances is true in the linear range portion of the PCR reaction. The final concentration of the target DNA in the plateau portion of the curve is determined by the availability of reagents in the reaction mix and is independent of the original concentration of target DNA. Therefore, the sampling and quantifying of the amplified PCR products may be carried out when the PCR reactions are in the linear portion of their curves. In addition, relative concentrations of the amplifiable cDNAs particularly are normalized to some independent standard, which may be based on either internally existing RNA species or externally introduced RNA species. The abundance of a particular mRNA species may also be determined relative to the average abundance of all mRNA species in the sample.

In one embodiment, the PCR amplification utilizes one or more internal PCR standards. The internal standard may be an abundant housekeeping gene in the cell or it can specifically be GAPDH, GUSB and β-2 microglobulin. These standards may be used to normalize expression levels so that the expression levels of different gene products can be compared directly. A person of ordinary skill in the art would know how to use an internal standard to normalize expression levels.

A problem inherent in clinical samples is that they are of variable quantity and/or quality. This problem can be overcome if the RT-PCR is performed as a relative quantitative RT-PCR with an internal standard in which the internal standard is an amplifiable cDNA fragment that is similar or larger than the target cDNA fragment and in which the abundance of the mRNA encoding the internal standard is roughly 5-100 fold higher than the mRNA encoding the target. This assay measures relative abundance, not absolute abundance of the respective mRNA species.

In another embodiment, the relative quantitative RT-PCR uses an external standard protocol. Under this protocol, the PCR products are sampled in the linear portion of their amplification curves. The number of PCR cycles that are optimal for sampling can be empirically determined for each target cDNA fragment. In addition, the reverse transcriptase products of each RNA population isolated from the various samples can be normalized for equal concentrations of amplifiable cDNAs.

Nucleic acid arrays can also be used to detect and compare the differential expression patterns of breast cancer biomarkers in breast cancer cells. The probes suitable for detecting the corresponding breast cancer biomarkers can be stably attached to known discrete regions on a solid substrate. As used herein, a probe is "stably attached" to a discrete region if the probe maintains its position relative to the discrete region during the hybridization and the subsequent washes. Construction of nucleic acid arrays is well known in the art. Suitable substrates for making polynucleotide arrays include, but are not limited to, membranes, films, plastics and quartz wafers.

A nucleic acid array can comprise at least or at most 1, 2, 3, 4, 5, 6, 7, 8, 9, 10, 15, 20, 25, 30, 35, 40, 45, 50, 60, 70, 80, 90, 100, 150, 200, 250 or more different polynucleotide probes (or any range derivable therein), which may hybridize to different and/or the same biomarkers. Multiple probes for the same gene can be used on a single nucleic acid array. Probes for other disease genes can also be included in the nucleic acid array. The probe density on the array can be in any range. In some embodiments, the density may be 50, 100, 200, 300, 400, 500 or more probes/cm$^2$.

Specifically contemplated are chip-based nucleic acid technologies such as those described by Hacia et al. (1996) and Shoemaker et al. (1996). Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization (see also, Pease et al., 1994; and Fodor et al, 1991). It is contemplated that this technology may be used in conjunction with evaluating the expression level of one or more breast cancer biomarkers with respect to diagnostic, prognostic, and treatment methods.

Certain embodiments may involve the use of arrays or data generated from an array. Data may be readily available. Moreover, an array may be prepared in order to generate data that may then be used in correlation studies.

An array generally refers to ordered macroarrays or microarrays of nucleic acid molecules (probes) that are fully or nearly complementary or identical to a plurality of mRNA molecules or cDNA molecules and that are positioned on a support material in a spatially separated organization. Macroarrays are typically sheets of nitrocellulose or nylon upon which probes have been spotted. Microarrays position the nucleic acid probes more densely such that up to 10,000 nucleic acid molecules can be fit into a region typically 1 to 4 square centimeters. Microarrays can be fabricated by spotting nucleic acid molecules, e.g., genes, oligonucleotides, etc., onto substrates or fabricating oligonucleotide sequences in situ on a substrate. Spotted or fabricated nucleic acid molecules can be applied in a high density matrix pattern of up to about 30 non-identical nucleic acid molecules per square centimeter or higher, e.g. up to about 100 or even 1000 per square centimeter. Microarrays typically use coated glass as the solid support, in contrast to the nitrocellulose-based material of filter arrays. By having an ordered array of complementing nucleic acid samples, the position of each sample can be tracked and linked to the original sample. A variety of different array devices in which a plurality of distinct nucleic acid probes are stably associated with the surface of a solid support are known to those of skill in the art. Useful substrates for arrays include nylon, glass and silicon. Such arrays may vary in a number of different ways, including average probe length, sequence or types of probes, nature of bond between the probe and the array surface, e.g. covalent or non-covalent, and the like. The labeling and screening methods and the arrays are not limited in its utility with respect to any parameter except that the probes detect expression levels; consequently, methods and compositions may be used with a variety of different types of genes.

Representative methods and apparatus for preparing a microarray have been described, for example, in U.S. Pat. Nos. 5,143,854; 5,202,231; 5,242,974; 5,288,644; 5,324,633; 5,384,261; 5,405,783; 5,412,087; 5,424,186; 5,429,807; 5,432,049; 5,436,327; 5,445,934; 5,468,613; 5,470,710; 5,472,672; 5,492,806; 5,525,464; 5,503,980; 5,510,270; 5,525,464; 5,527,681; 5,529,756; 5,532,128; 5,545,531; 5,547,839; 5,554,501; 5,556,752; 5,561,071; 5,571,639; 5,580,726; 5,580,732; 5,593,839; 5,599,695; 5,599,672; 5,610,287; 5,624,711; 5,631,134; 5,639,603; 5,654,413; 5,658,734; 5,661,028; 5,665,547; 5,667,972; 5,695,940; 5,700,637; 5,744,305; 5,800,992; 5,807,522; 5,830,645; 5,837,196; 5,871,928; 5,847,219; 5,876,932; 5,919,626; 6,004,755; 6,087,102; 6,368,799; 6,383,749; 6,617,112; 6,638,717; 6,720,138, as well as WO 93/17126; WO 95/11995; WO 95/21265; WO 95/21944; WO 95/35505; WO 96/31622; WO 97/10365; WO 97/27317; WO 99/35505; WO 09923256; WO 09936760; WO0138580; WO 0168255; WO 03020898; WO 03040410; WO 03053586; WO 03087297; WO 03091426; WO03100012; WO 04020085; WO 04027093; EP 373 203; EP 785 280; EP 799 897 and UK 8 803 000; the disclosures of which are all herein incorporated by reference.

It is contemplated that the arrays can be high density arrays, such that they contain 100 or more different probes. It is contemplated that they may contain 1000, 16,000, 65,000, 250,000 or 1,000,000 or more different probes. The probes can be directed to targets in one or more different organisms. The oligonucleotide probes range from 5 to 50, 5 to 45, 10 to 40, or 15 to 40 nucleotides in length in some embodiments. In certain embodiments, the oligonucleotide probes are 20 to 25 nucleotides in length.

The location and sequence of each different probe sequence in the array are generally known. Moreover, the large number of different probes can occupy a relatively small area providing a high density array having a probe density of generally greater than about 60, 100, 600, 1000, 5,000, 10,000, 40,000, 100,000, or 400,000 different oligonucleotide probes per $cm^2$. The surface area of the array can be about or less than about 1, 1.6, 2, 3, 4, 5, 6, 7, 8, 9, or 10 $cm^2$.

Moreover, a person of ordinary skill in the art could readily analyze data generated using an array. Such protocols include information found in WO 9743450; WO 03023058; WO 03022421; WO 03029485; WO 03067217; WO 03066906; WO 03076928; WO 03093810; WO 03100448A1, all of which are specifically incorporated by reference.

In one embodiment, nuclease protection assays are used to quantify RNAs derived from the breast cancer samples. There are many different versions of nuclease protection assays known to those practiced in the art. The common characteristic that these nuclease protection assays have is that they involve hybridization of an antisense nucleic acid with the RNA to be quantified. The resulting hybrid double-stranded molecule is then digested with a nuclease that digests single-stranded nucleic acids more efficiently than double-stranded molecules. The amount of antisense nucleic acid that survives digestion is a measure of the amount of the target RNA species to be quantified. An example of a nuclease protection assay that is commercially available is the RNase protection assay manufactured by Life Technologies, Inc.

B. Proteins and Polypeptides

In other embodiments, the differential expression patterns of breast cancer biomarkers can be determined by measuring the levels of polypeptides encoded by these genes in breast cancer cells. Methods suitable for this purpose include, but are not limited to, immunoassays such as ELISA, RIA, FACS, dot blot, Western Blot, immunohistochemistry, and antibody-based radioimaging. Protocols for carrying out these immunoassays are well known in the art. Other methods such as 2-dimensional SDS-polyacrylamide gel electrophoresis can also be used. These procedures may be used to recognize any of the polypeptides encoded by the breast cancer biomarker genes described herein.

One example of a method suitable for detecting the levels of target proteins in peripheral blood samples is ELISA. In an exemplifying ELISA, antibodies capable of binding to the target proteins encoded by one or more breast cancer biomarker genes are immobilized onto a selected surface exhibiting protein affinity, such as wells in a polystyrene or polyvinylchloride microtiter plate. Then, breast cancer cell samples to be tested are added to the wells. After binding and washing to remove non-specifically bound immunocomplexes, the bound antigen(s) can be detected. Detection can be achieved by the addition of a second antibody which is specific for the target proteins and is linked to a detectable label. Detection may also be achieved by the addition of a second antibody, followed by the addition of a third antibody that has binding affinity for the second antibody, with the third antibody being linked to a detectable label. Before being added to the microtiter plate, cells in the peripheral blood samples can be lysed using various methods known in the art. Proper extraction procedures can be used to separate the target proteins from potentially interfering substances.

In another ELISA embodiment, the breast cancer cell samples containing the target proteins are immobilized onto the well surface and then contacted with the antibodies. After binding and washing to remove non-specifically bound immunocomplexes, the bound antigen is detected. Where the initial antibodies are linked to a detectable label, the immunocomplexes can be detected directly. The immunocomplexes can also be detected using a second antibody that has binding affinity for the first antibody, with the second antibody being linked to a detectable label.

Another typical ELISA involves the use of antibody competition in the detection. In this ELISA, the target proteins are immobilized on the well surface. The labeled antibodies are added to the well, allowed to bind to the target proteins, and detected by means of their labels. The amount of the target proteins in an unknown sample is then determined by mixing the sample with the labeled antibodies before or during incubation with coated wells. The presence of the target proteins in the unknown sample acts to reduce the amount of antibody available for binding to the well and thus reduces the ultimate signal.

Different ELISA formats can have certain features in common, such as coating, incubating or binding, washing to remove non-specifically bound species, and detecting the bound immunocomplexes. For instance, in coating a plate with either antigen or antibody, the wells of the plate can be incubated with a solution of the antigen or antibody, either overnight or for a specified period of hours. The wells of the plate are then washed to remove incompletely adsorbed material. Any remaining available surfaces of the wells are then "coated" with a nonspecific protein that is antigenically neutral with regard to the test samples. Examples of these nonspecific proteins include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, a secondary or tertiary detection means can also be used. After binding of a protein or antibody to the well, coating with a non-reactive material to reduce background, and washing to remove unbound material, the immobilizing surface is contacted with the control and/or clinical or biological sample to be tested under conditions effective to allow immunocomplex (antigen/antibody) formation. These conditions may include, for example, diluting the antigens and antibodies with solutions such as BSA, bovine gamma globulin (BGG) and phosphate buffered saline (PBS)/Tween and incubating the antibodies and antigens at room temperature for about 1 to 4 hours or at 49° C. overnight. Detection of the immunocomplex then requires a labeled secondary binding ligand or antibody, or a secondary binding ligand or antibody in conjunction with a labeled tertiary antibody or third binding ligand.

After all of the incubation steps in an ELISA, the contacted surface can be washed so as to remove non-complexed material. For instance, the surface may be washed with a solution such as PBS/Tween, or borate buffer. Following the formation of specific immunocomplexes between the test sample and the originally bound material, and subsequent washing, the occurrence of the amount of immunocomplexes can be determined.

To provide a detecting means, the second or third antibody can have an associated label to allow detection. In one embodiment, the label is an enzyme that generates color development upon incubating with an appropriate chromogenic substrate. Thus, for example, one may contact and incubate the first or second immunocomplex with a urease, glucose oxidase, alkaline phosphatase or hydrogen peroxidase-conjugated antibody for a period of time and under conditions that favor the development of further immunocomplex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple or 2,2'-azido-di-(3-ethyl)-benzhiazoline-6-sulfonic acid (ABTS) and hydrogen peroxide, in the case of peroxidase as the enzyme label. Quantitation can be achieved by measuring the degree of color generation, e.g., using a spectrophotometer.

Another suitable method is RIA (radioimmunoassay). An example of RIA is based on the competition between radiolabeled-polypeptides and unlabeled polypeptides for binding to a limited quantity of antibodies. Suitable radiolabels include, but are not limited to, $I^{125}$. In one embodiment, a fixed concentration of $I^{125}$-labeled polypeptide is incubated with a series of dilution of an antibody specific to the polypeptide. When the unlabeled polypeptide is added to the system, the amount of the $I^{125}$-polypeptide that binds to the antibody is decreased. A standard curve can therefore be constructed to represent the amount of antibody-bound $I^{125}$-polypeptide as a function of the concentration of the unlabeled polypeptide. From this standard curve, the concentration of the polypeptide in unknown samples can be determined. Various protocols for conducting RIA to measure the levels of polypeptides in breast cancer cell samples are well known in the art.

Suitable antibodies include, but are not limited to, polyclonal antibodies, monoclonal antibodies, chimeric antibodies, humanized antibodies, single chain antibodies, Fab fragments, and fragments produced by a Fab expression library.

Antibodies can be labeled with one or more detectable moieties to allow for detection of antibody-antigen complexes. The detectable moieties can include compositions detectable by spectroscopic, enzymatic, photochemical, biochemical, bioelectronic, immunochemical, electrical, optical or chemical means. The detectable moieties include, but are not limited to, radioisotopes, chemiluminescent compounds, labeled binding proteins, heavy metal atoms, spectroscopic markers such as fluorescent markers and dyes, magnetic labels, linked enzymes, mass spectrometry tags, spin labels, electron transfer donors and acceptors, and the like.

Protein array technology is discussed in detail in Pandey and Mann (2000) and MacBeath and Schreiber (2000), each of which is herein specifically incorporated by reference. These arrays typically contain thousands of different proteins or antibodies spotted onto glass slides or immobilized in tiny wells and allow one to examine the biochemical activities and binding profiles of a large number of proteins at once. To examine protein interactions with such an array, a labeled protein is incubated with each of the target proteins immobilized on the slide, and then one determines which of the many proteins the labeled molecule binds. In certain embodiments such technology can be used to quantitate a number of proteins in a sample, such as a breast cancer biomarker proteins.

The basic construction of protein chips has some similarities to DNA chips, such as the use of a glass or plastic surface dotted with an array of molecules. These molecules can be DNA or antibodies that are designed to capture proteins. Defined quantities of proteins are immobilized on each spot, while retaining some activity of the protein. With fluorescent markers or other methods of detection revealing the spots that have captured these proteins, protein microarrays are being used as powerful tools in high-throughput proteomics and drug discovery.

The earliest and best-known protein chip is the ProteinChip by Ciphergen Biosystems Inc. (Fremont, Calif.). The ProteinChip is based on the surface-enhanced laser desorption and ionization (SELDI) process. Known proteins are analyzed using functional assays that are on the chip. For example, chip surfaces can contain enzymes, receptor proteins, or antibodies that enable researchers to conduct protein-protein interaction studies, ligand binding studies, or immunoassays. With state-of-the-art ion optic and laser optic technologies, the ProteinChip system detects proteins ranging from small peptides of less than 1000 Da up to proteins of 300 kDa and calculates the mass based on time-of-flight (TOF).

The ProteinChip biomarker system is the first protein biochip-based system that enables biomarker pattern recognition analysis to be done. This system allows researchers to address important clinical questions by investigating the proteome from a range of crude clinical samples (i.e., laser capture microdissected cells, biopsies, tissue, urine, and serum). The system also utilizes biomarker pattern software that automates pattern recognition-based statistical analysis methods to correlate protein expression patterns from clinical samples with disease phenotypes.

In other aspects, the levels of polypeptides in samples can be determined by detecting the biological activities associated with the polypeptides. If a biological function/activity of a polypeptide is known, suitable in vitro bioassays can be designed to evaluate the biological function/activity, thereby determining the amount of the polypeptide in the sample.

II. Breast Cancer Therapy

Certain embodiments are directed to methods of treating breast cancer based on GR and/or AR status of the breast cancer tissue. In some embodiments, a breast cancer that is characterized as triple negative is specifically amenable to treatment with an Hsp90 inhibitor with or without chemotherapy. In some embodiments, the hormone receptor status is determined based on the expression of a hormone receptor such as the androgen receptor (AR) in combination with the glucocorticoid receptor (GR).

In certain aspects, there may be provided methods for treating a subject determined to have cancer and with a predetermined expression profile of one or more biomarkers disclosed herein.

In a further aspect, biomarkers and related systems that can establish a prognosis of cancer patients can be used to identify patients who may get benefit of conventional single or combined modality therapy. In the same way, those patients who do not get much benefit from such conventional single or combined modality therapy can be identified and can be offered alternative treatment(s).

In certain aspects, conventional cancer therapy may be applied to a subject wherein the subject is identified or reported as having a good prognosis based on the assessment of the biomarkers as disclosed. On the other hand, at least an alternative cancer therapy may be prescribed, as used alone or in combination with conventional cancer therapy, if a poor prognosis is determined by the disclosed methods, systems, or kits.

Embodiments concern an Hsp90 inhibitor. It is specifically contemplated that one or more of the Hsp90 inhibitor discussed herein or in the incorporated references may be excluded in certain embodiments. It is also contemplated that in some embodiments, more than one Hsp90 inhibitor is employed, while in other embodiments, only one is employed as part of the therapeutic method (though it may be administered multiple times). It is contemplated that the second one may be administered concurrently with the first one or they may be administered at different times.

Conventional cancer therapies include one or more selected from the group of chemical or radiation based treatments and surgery. Chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabine, navelbine, farnesyl-protein transferase inhibitors, transplatinum, 5-fluorouracil, vincristin, vinblastin and methotrexate, or any analog or derivative variant of the foregoing.

Suitable therapeutic agents include, for example, vinca alkaloids, agents that disrupt microtubule formation (such as colchicines and its derivatives), anti-angiogenic agents, therapeutic antibodies, EGFR targeting agents, tyrosine kinase targeting agent (such as tyrosine kinase inhibitors), serine kinase targeting agents, transitional metal complexes, proteasome inhibitors, antimetabolites (such as nucleoside analogs), alkylating agents, platinum-based agents, anthracycline antibiotics, topoisomerase inhibitors, macrolides, therapeutic antibodies, retinoids (such as all-trans retinoic acids or a derivatives thereof); geldanamycin or a derivative thereof (such as 17-AAG), and other standard chemotherapeutic agents well recognized in the art.

Certain chemotherapeutics are well known for use against breast cancer. These breast cancer chemotherapeutics are capecitabine, carboplatin, cyclophosphamide (Cytoxan), daunorubicin, docetaxel (Taxotere), doxorubicin (Adriamycin), epirubicin (Ellence), fluorouracil (also called 5-fluorouracil or 5-FU), gemcitabine, eribulin, ixabepilone, methotrexate, mitomycin C, mitoxantrone, paclitaxel (Taxol), thiotepa, vincristine, vinorelbine.

In some embodiments, the chemotherapeutic agent is any of (and in some embodiments selected from the group consisting of) adriamycin, colchicine, cyclophosphamide, actinomycin, bleomycin, daunorubicin, doxorubicin, epirubicin, mitomycin, methotrexate, mitoxantrone, fluorouracil, carboplatin, carmustine (BCNU), methyl-CCNU, cisplatin, etoposide, interferons, camptothecin and derivatives thereof, phenesterine, taxanes and derivatives thereof (e.g., paclitaxel and derivatives thereof, taxotere and derivatives thereof, and the like), topetecan, vinblastine, vincristine, tamoxifen, piposulfan, nab-5404, nab-5800, nab-5801, Irinotecan, HKP, Ortataxel, gemcitabine, Herceptin®, vinorelbine, capecitabine, Gleevec®, Alimta®, Avastin®, Velcade®, Tarceva®, Neulasta®, Lapatinib, STI-571, ZD1839, Iressa® (gefitinib), SH268, genistein, CEP2563, SU6668, SU11248, EMD121974, and Sorafenib.

In some embodiments, the chemotherapeutic agent is a composition comprising nanoparticles comprising a thio-colchicine derivative and a carrier protein (such as albumin).

In further embodiments a combination of chemotherapeutic agents is administered to breast cancer cells. The chemotherapeutic agents may be administered serially (within minutes, hours, or days of each other) or in parallel; they also may be administered to the patient in a pre-mixed single composition. The composition may or may not contain an Hsp90 inhibitor. Combinations of breast cancer therapeutics include, but are not limited to the following: AT (Adriamycin and Taxotere), AC±T: (Adriamycin and Cytoxan, with or without Taxol or Taxotere), CMF (Cytoxan, methotrexate, and fluorouracil), CEF (Cytoxan, Ellence, and fluorouracil), FAC (fluorouracil, Adriamycin, and Cytoxan), CAF (Cytoxan, Adriamycin, and fluorouracil) (the FAC and CAF regimens use the same medicines but use different doses and frequencies), TAC (Taxotere, Adriamycin, and Cytoxan), and GET (Gemzar, Ellence, and Taxol). In some embodiments trastuzumab (Herceptin®) is administered to a breast cancer patient with an Hsp90 inhibitor, which may be with or without a chemotherapeutic or a combination of chemotherapeutics.

Various combinations with an Hsp90 inhibitor and an anticancer agent or compound (or a combination of such agents and/or compounds) may be employed, for example, an Hsp90 inhibitor is "A" and the anticancer agent or compound (or a combination of such agents and/or compounds) given as part of an anticancer therapy regime, is "B":

| | | | | | |
|---|---|---|---|---|---|
| A/B/A | B/A/B | B/B/A | A/A/B | A/B/B | B/A/A |
| A/B/B/B | B/A/B/B | B/B/B/A | B/B/A/B | A/A/B/B | A/B/A/B |
| A/B/B/A | B/B/A/A | B/A/B/A | B/A/A/B | A/A/A/B | B/A/A/A |
| A/B/A/A | A/A/B/A | | | | |

Administration of the therapeutic compounds or agents to a patient will follow general protocols for the administration of such compounds, taking into account the toxicity, if any, of the therapy. It is expected that the treatment cycles would be repeated as necessary. It also is contemplated that various standard therapies, as well as surgical intervention, may be applied in combination with the described therapy.

The term "a serine/threonine kinase inhibitor", as used herein, relates to a compound which inhibits serine/threonine kinases. An example of a target of a serine/threonine kinase inhibitor includes, but is not limited to, dsRNA-dependent protein kinase (PKR). Examples of indirect targets of a serine/threonine kinase inhibitor include, but are not limited to, MCP-1, NF-kappaB, eIF2alpha, COX2, RANTES, IL8, CYP2A5, IGF-1, CYP2B1, CYP2B2, CYP2H1, ALAS-1, HIF-1, erythropoietin and/or CYP1A1. An example of a serine/theronin kinase inhibitor includes, but is not limited to, Sorafenib and 2-aminopurine, also known as 1H-purin-2-amine(9CI). Sorafenib is marketed as NEXAVAR.

The term "an angiogenesis inhibitor", as used herein, relates to a compound which targets, decreases or inhibits the production of new blood vessels. Targets of an angiogenesis inhibitor include, but are not limited to, methionine aminopeptidase-2 (MetAP-2), macrophage inflammatory protein-1 (MIP-1a), CCL5, TGF-β, lipoxygenase, cyclooxygenase, and topoisomerase. Indirect targets of an angiogenesis inhibitor include, but are not limited to, p21, p53, CDK2 and collagen synthesis. Examples of an angiogenesis inhibitor include, but are not limited to, Fumagillin, which is known as 2,4,6,8-decatetraenedioic acid, mono[3R,4S,5 S,6R)-5-methoxy-4-[(2R,3R)-2-methyl-3-(3-methyl-2-butenyl)oxi-ranyl]-1-oxaspiro[2.5]oct-6-yl]ester, (2E,4E,6E, 8E)-(9CI); Shikonin, which is also known as 1,4-naphthalenedione, 5, 8-dihydroxy-2-[(1R)-1-hydroxy-4-methyl-3-pentenyl]-(9CI); Tranilast, which is also known as benzoic acid, 2-[[3-(3,4-dimethoxyphenyl)-1-oxo-2-propenyl] amino]-(9CI); ursolic acid; suramin; thalidomide and lenalidomide, and marketed as REVLIMID.

Radiation therapy that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

Approximately 60% of persons with cancer will undergo surgery of some type, which includes preventative, diagnostic or staging, curative and palliative surgery. Curative surgery is a cancer treatment that may be used in conjunction with other therapies, such as the treatment, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the treatment methods described herein may be used in conjunction with removal of superficial cancers, precancers, or incidental amounts of normal tissue.

Laser therapy is the use of high-intensity light to destroy tumor cells. Laser therapy affects the cells only in the treated area. Laser therapy may be used to destroy cancerous tissue and relieve a blockage in the esophagus when the cancer cannot be removed by surgery. The relief of a blockage can help to reduce symptoms, especially swallowing problems.

Photodynamic therapy (PDT), a type of laser therapy, involves the use of drugs that are absorbed by cancer cells; when exposed to a special light, the drugs become active and destroy the cancer cells. PDT may be used to relieve symptoms of esophageal cancer such as difficulty swallowing.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well. A patient may be administered a single compound (such as an Hsp90 inhibitor or a chemotherapeutic) or a combination of compounds described herein in an amount that is, is at least, or is at most 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg/kg (or any range derivable therein). A patient may be administered a single compound or a combination of compounds described herein in an amount that is, is at least, or is at most 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500 mg/kg/day (or any range derivable therein).

Alternative cancer therapy include any cancer therapy other than surgery, chemotherapy and radiation therapy, such as immunotherapy, gene therapy, hormonal therapy or a combination thereof. Subjects identified with poor prognosis using the present methods may not have favorable response to conventional treatment(s) alone and may be prescribed or administered one or more alternative cancer therapy per se or in combination with one or more conventional treatments.

For example, the alternative cancer therapy may be a targeted therapy. The targeted therapy may be an anti-EGFR treatment. In one embodiment of the method, the anti-EGFR agent used is a tyrosine kinase inhibitor. Examples of suitable tyrosine kinase inhibitors are the quinazoline derivatives described in WO 96/33980, in particular gefitinib (Iressa). Other examples include quinazoline derivatives described in WO 96/30347, in particular erlotinib (Tarceva), dual EGFR/HER2 tyrosine kinase inhibitors, such as lapatinib, or pan-Erb inhibitors. In a particular embodiment of the method or use, the anti-EGFR agent is an antibody capable of binding to EGFR, i.e. an anti-EGFR antibody.

In a further embodiment, the anti-EGFR antibody is an intact antibody, i.e. a full-length antibody rather than a fragment. An anti-EGFR antibody used in the method may have any suitable affinity and/or avidity for one or more epitopes contained at least partially in EGFR. Particularly, the antibody used binds to human EGFR with an equilibrium dissociation constant ($K_D$) of $10^{-8}$ M or less, more particularly $10^{-10}$ M or less.

Particularly antibodies for use include zalutumumab (2F8), cetuximab (Erbitux), nimotuzumab (h-R3), panitumumab (ABX-EGF), and matuzumab (EMD72000), or a variant antibody of any of these, or an antibody that is able to compete with any of these, such as an antibody recognizing the same epitope as any of these. Competition may be determined by any suitable technique. In one embodiment, competition is determined by an ELISA assay. Often competition is marked by a significantly greater relative inhibition than 5% as determined by ELISA analysis.

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Gene therapy is the insertion of polynucleotides, including DNA or RNA, into an individual's cells and tissues to treat a disease. Antisense therapy is also a form of gene therapy. A therapeutic polynucleotide may be administered before, after, or at the same time of a first cancer therapy. Delivery of a vector encoding a variety of proteins is encompassed in certain aspects. For example, cellular expression of the exogenous tumor suppressor oncogenes would exert their function to inhibit excessive cellular proliferation, such as p53, p16 and C-CAM.

Additional agents to be used to improve the therapeutic efficacy of treatment include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with treatment methods described herein to improve the anti-hyperproliferative efficacy of the treatments Inhibitors of cell adhesion are contemplated to improve the efficacy. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with treatment methods described herein to improve the treatment efficacy.

Hormonal therapy may also be used or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

II. Circulating Tumor Cells

In certain embodiments, circulating tumor cells may be evaluated or tested. Circulating tumor cells (CTCs) are cells that have shed into the vasculature from a primary or metastatic tumor and circulate in the bloodstream. CTCs thus constitute seeds for subsequent growth of additional tumors (metastasis) in vital distant organs, triggering a mechanism that is responsible for the vast majority of cancer-related deaths.

Several methods have been developed to detect circulating tumor cells. This CellSearch method is based on the use of iron nano-particles coated with a polymer layer carrying biotin analogues and conjugated with antibodies anti EpCAM for capturing CTCs, and on the use of an analyzer to take images of isolated cells upon their staining with specific fluorescent antibody conjugates. Another methods, the Epic Sciences method, involves technology to separate nucleated cells from red blood cells, which lack a nucleus.

Biological methods are separation based on antigen-antibody bindings. Antibodies against tumor specific biomarkers including EpCAM, Her2, PSA are used. The most common technique is magnetic nanoparticle-based separation (immunomagnetic assay) as used in CellSearch or MACS. Other techniques under research include microfluidic separation and combination of immunomagnetic assay and microfluidic separation. Oncolytic viruses such as vacinia viruses are developed to detect and identify CTCs.

Physical methods are often filter-based, enabling the capture of CTCs by size. ScreenCell is a filtration-based device that allows sensitive and specific isolation of CTCs from human whole blood in a few minutes. Peripheral blood is drawn and processed within 4 hours with a ScreenCell isolation device to capture CTCs. The captured cells are ready for cell culture or for direct characterization using ViewRNA in situ hybridization assay.

III. Kits

Certain aspects also encompass kits for performing the diagnostic or therapeutic methods. Such kits can be prepared from readily available materials and reagents. For example, such kits can comprise any one or more of the following materials: enzymes, reaction tubes, buffers, detergent, primers, probes, antibodies. In a particular embodiment, these kits allow a practitioner to obtain samples of neoplastic cells in breast, blood, tears, semen, saliva, urine, tissue, serum, stool, sputum, cerebrospinal fluid and supernatant from cell lysate. In another particular embodiment, these kits include the needed apparatus for performing RNA extraction, RT-PCR, and gel electrophoresis. Instructions for performing the assays can also be included in the kits.

In a particular aspect, these kits may comprise a plurality of agents for assessing the differential expression of a plurality of biomarkers, for example, GR and/or AR, wherein the kit is housed in a container. The kits may further comprise instructions for using the kit for assessing expression, means for converting the expression data into expression values and/or means for analyzing the expression values to generate prognosis. The agents in the kit for measuring biomarker expression may comprise a plurality of PCR probes and/or primers for qRT-PCR and/or a plurality of antibody or fragments thereof for assessing expression of the biomarkers. In another embodiment, the agents in the kit for measuring biomarker expression may comprise an array of polynucleotides complementary to the mRNAs of the biomarkers. Possible means for converting the expression data into expression values and for analyzing the expression values to generate scores that predict survival or prognosis may be also included.

Kits may comprise a container with a label. Suitable containers include, for example, bottles, vials, and test tubes. The containers may be formed from a variety of materials such as glass or plastic. The container may hold a composition which includes a probe that is useful for prognostic or non-prognostic applications, such as described above. The label on the container may indicate that the composition is used for a specific prognostic or non-prognostic application, and may also indicate directions for either in vivo or in vitro use, such as those described above. The kit may comprise the container described above and one or more other containers comprising materials desirable from a commercial and user standpoint, including buffers, diluents, filters, needles, syringes, and package inserts with instructions for use.

EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of particular embodiments, are exemplary, and are not intended as limitations on the scope of the invention. Changes therein and other uses which are encompassed within the spirit of the invention as defined by the scope of the claims will occur to those skilled in the art.

Example 1

Materials and Methods

TNBC cell lines were pre-treated for 2 hours with dexamethasone (100 nM) followed by ganetespib (50 nM). Protein and transcript levels were analyzed using Western blot and qRT-PCR respectively.

TNBC cell lines were treated with paclitaxel (10 nM) and ganetespib (50 nM) and cell death was monitored by staining with a fluorescent DNA binding dye followed by Incucyte live cell imaging. An Image J macro was written to count fluorescent dead cells and total cell number (phase contrast images). The % cell death was then calculated from the ratio of fluorescent dead/total cells (9).

Six week old SCID female mice were injected in the mammary fat pad with MDA-MB-231 cells. When tumors reached a volume of 150 mm$^3$, mice were treated with ganetespib, paclitaxel or the combination once a week for 3 weeks. Tumor volumes were measured throughout the experiment and at the culmination tumors were removed, weighed and protein lysates prepared for Western blot analysis.

Example 2

Hsp90 Inhibition Results in Proteasome-Mediated Degradation of Both GR and AR

Figures 4A, 4B:
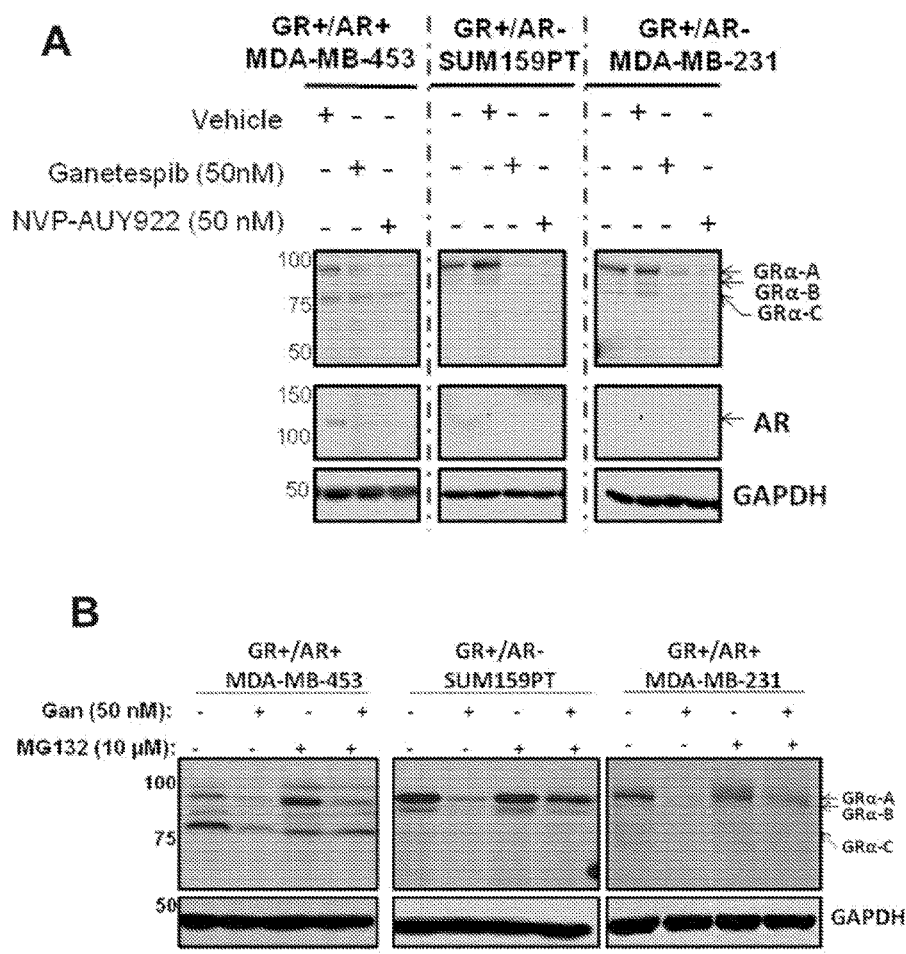
FIG. 4A. GR-α translational isoforms and AR protein are both depleted following Hsp90 inhibitor treatment (50 nM ganetespib or NVP-AUY922, 8 hrs) of TNBC cell lines.
FIG. 4B. Depletion of GR following Hsp90 inhibitor treatment (8 hours) is partially reversed following treatment of ganetespib (50 nM) with the proteasome inhibitor MG132 (10 μM) for 6 hours.
Figure 5A:
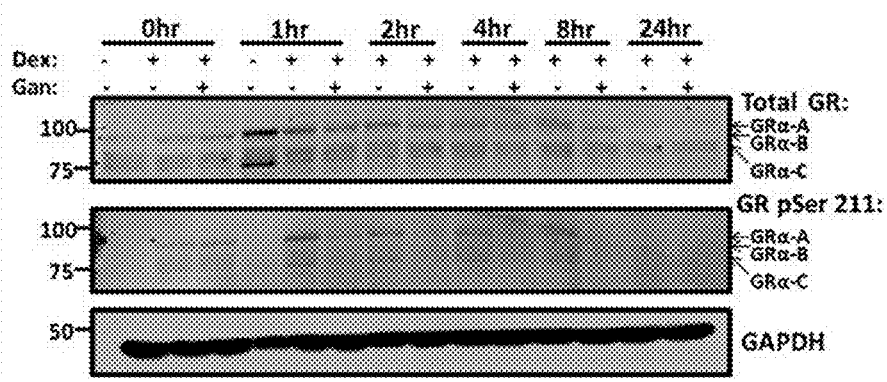
FIG. 5A-5C GR target gene transcripts (SGK1 and MKP1) were induced after treatment with 100 nM dexamethasone (dex) for 2 hours. This induction was reduced following ganetespib (50 nM) treatment.
Figure 5A:
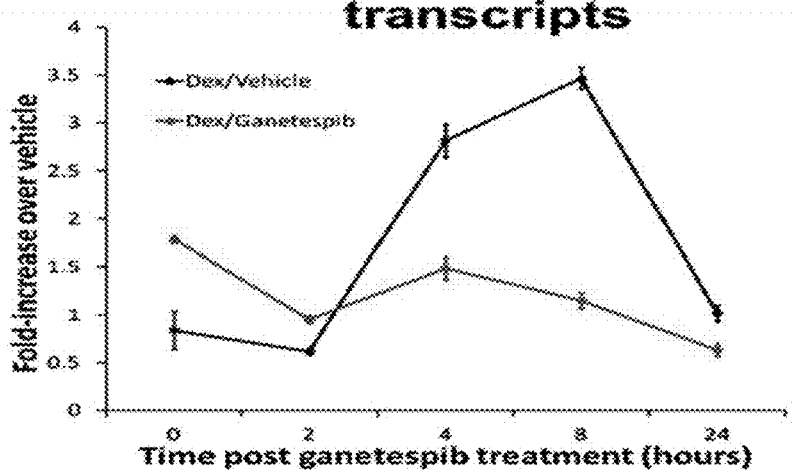
Figure 5A:
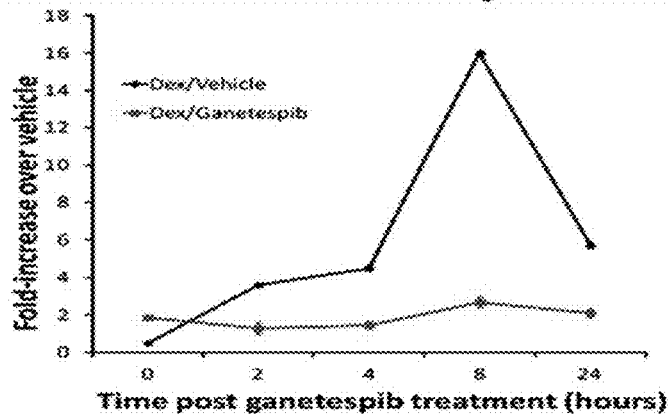
Figure 5B:
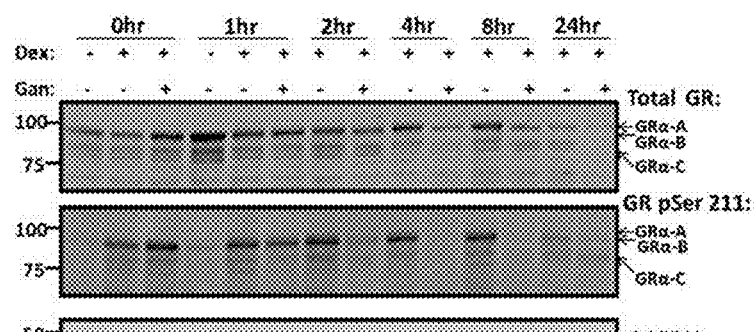
Figure 5B:
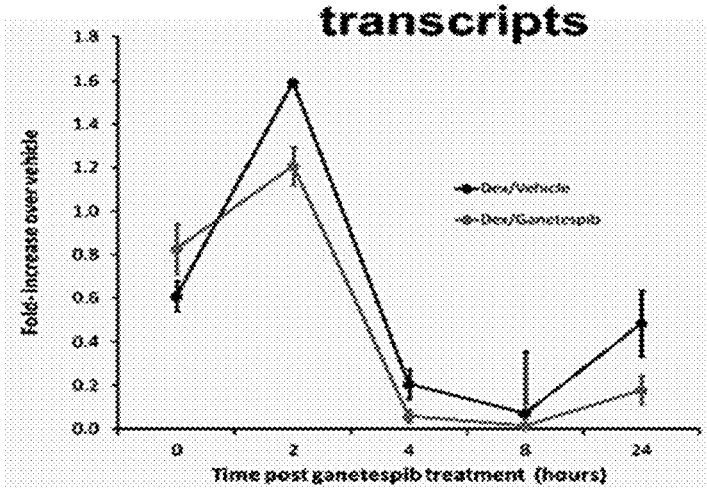
Figure 5B:
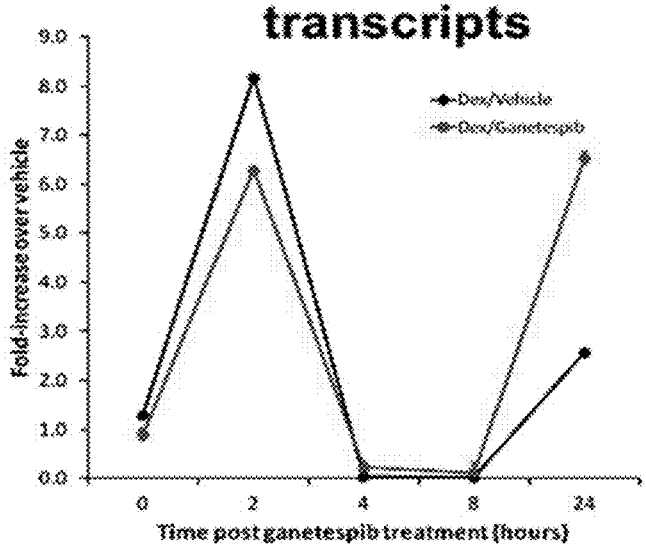
Figure 5C:
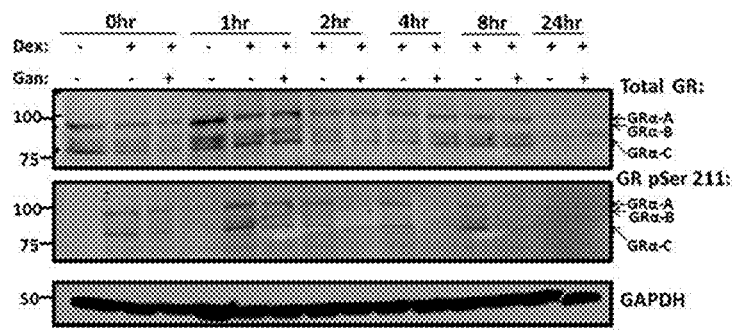
Figure 5C:
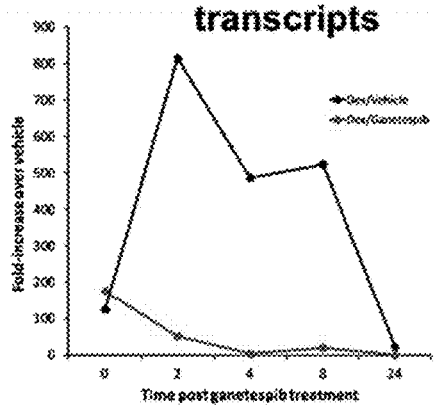
Figure 5C:
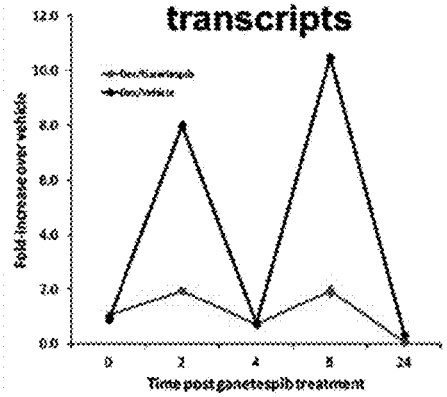
Figure 5C:
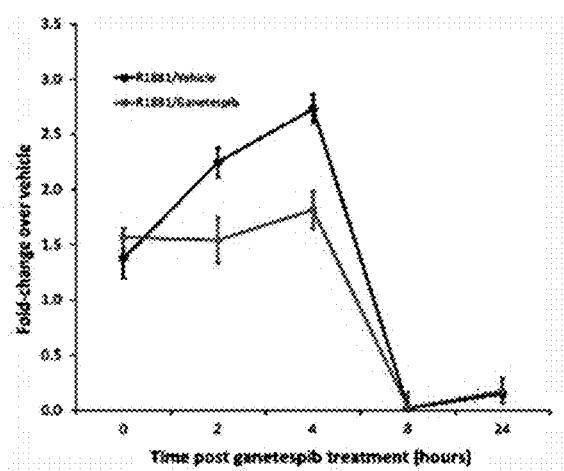

FIG. 4A shows that GR-α translational isoforms and AR protein are both depleted following Hsp90 inhibitor treatment (50 nM ganetespib or NVP-AUY922, 8 hrs) of TNBC cell lines. FIG. 4B shows depletion of GR following Hsp90 inhibitor treatment (8 hours) is partially reversed following treatment of ganetespib (50 nM) with the proteasome inhibitor MG132 (10 µM) for 6 hours.

Example 3

GR and AR Transcriptional Activity is Decreased Following Hsp90 Inhibitor Treatment Overexpress GR in GR-Depleted Cells to Confirm the Requirement for GR in Hsp90 Inhibitor Mediated Sensitization of TNBC Cells to Paclitaxel.

FIG. 5 shows that GR target gene transcripts (SGK1 and MKP1/DUSP1) were induced after treatment with 100 nM dexamethasone (dex) for 2 hours. This induction was reduced following ganetespib (50 nM) treatment. FIG. 5C shows that androgen (R1881, 1 nM) pre-treatment for 2 hours also induced expression of the AR target gene TMPRSS2 which was decreased by concomitant ganetespib (50 nM) treatment.

Example 4

Figures 6A, 6B, 6C, 6D:
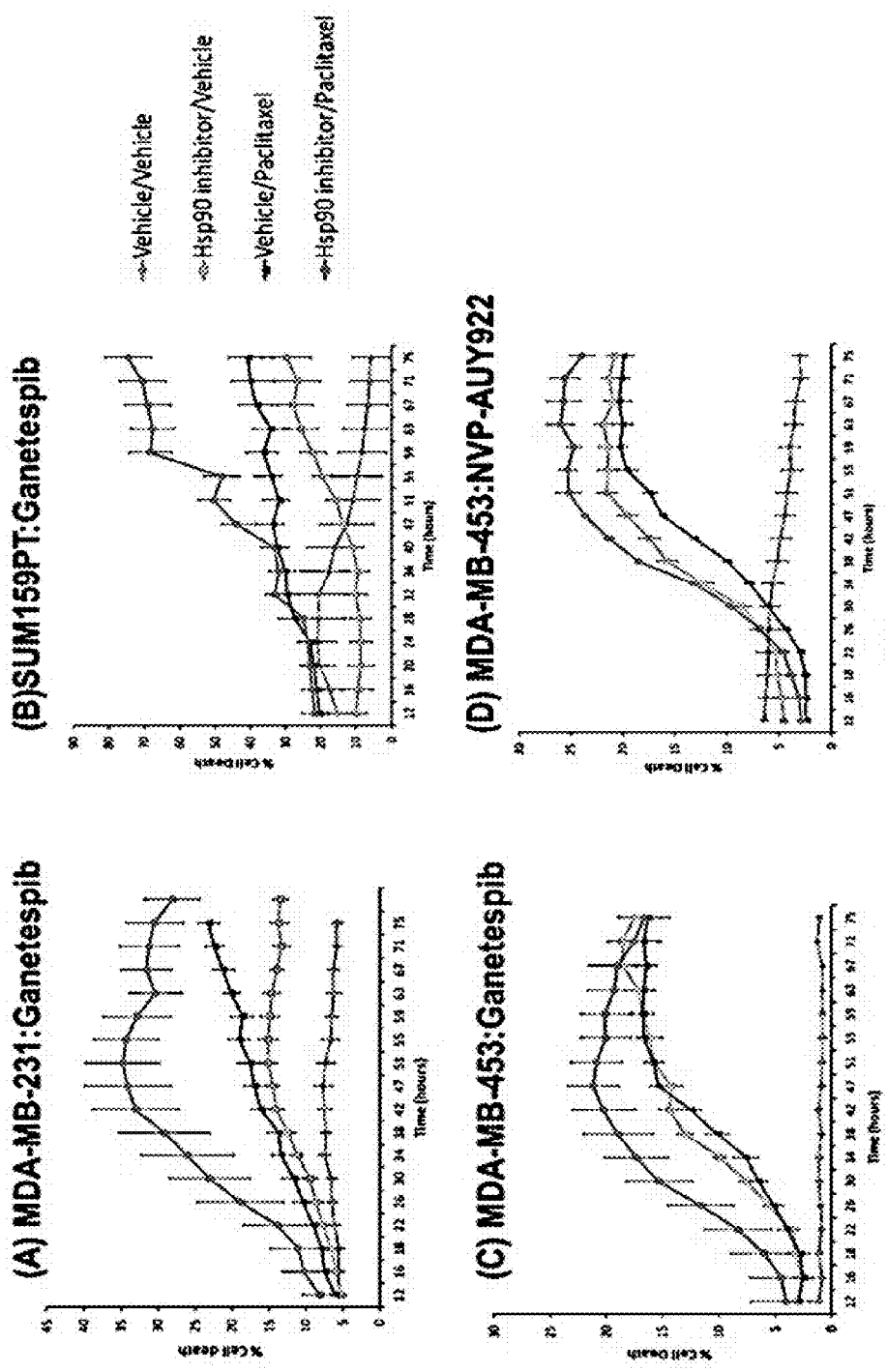
FIGS. 6A-6D Incucyte live cell imaging of TNBC cell lines showing increased cell death of cells treated with ganetespib (50 nM) and paclitaxel (10 nM) compared to either drug alone.

Treatment with Paclitaxel and an Hsp90 Inhibitor Causes Increased TNBC Cell Death FIG. 6 A-D shows Incucyte live cell imaging of TNBC cell lines showing increased cell death of cells treated with ganetespib (50 nM) and paclitaxel (10 nM) compared to either drug alone.

Example 5

Figures 7A, 7B:
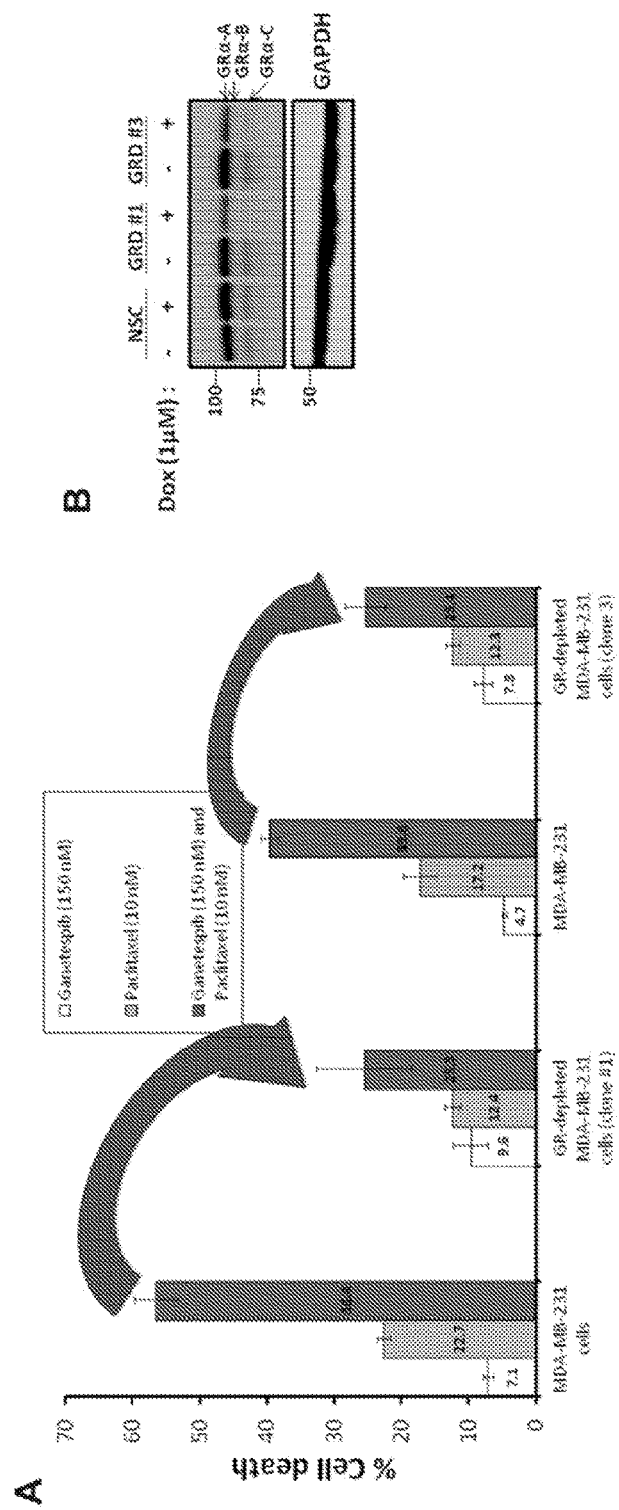
FIGS. 7A-7B.

GR Expression is Required for Increased Cell Death Following Addition of Hsp90 Inhibitor to Paclitaxel In Vitro FIG. 7A shows that ganetespib (150 nM) and paclitaxel (10 nM) is not synergistic in GR-depleted MDA-MB-231 cells demonstrating the requirement for GR. Cells death was analyzed by the mitochondrial membrane potential assay. FIG. 7B shows that doxycycline (dox)-inducible GR-depleted MDA-MB-231 cells (clone #1=GRD#1 and clone 3) and MDA-MB-231 GR-intact non silencing control (NSC) were established for the experiments in A.

Example 6

Figures 8A, 8B:
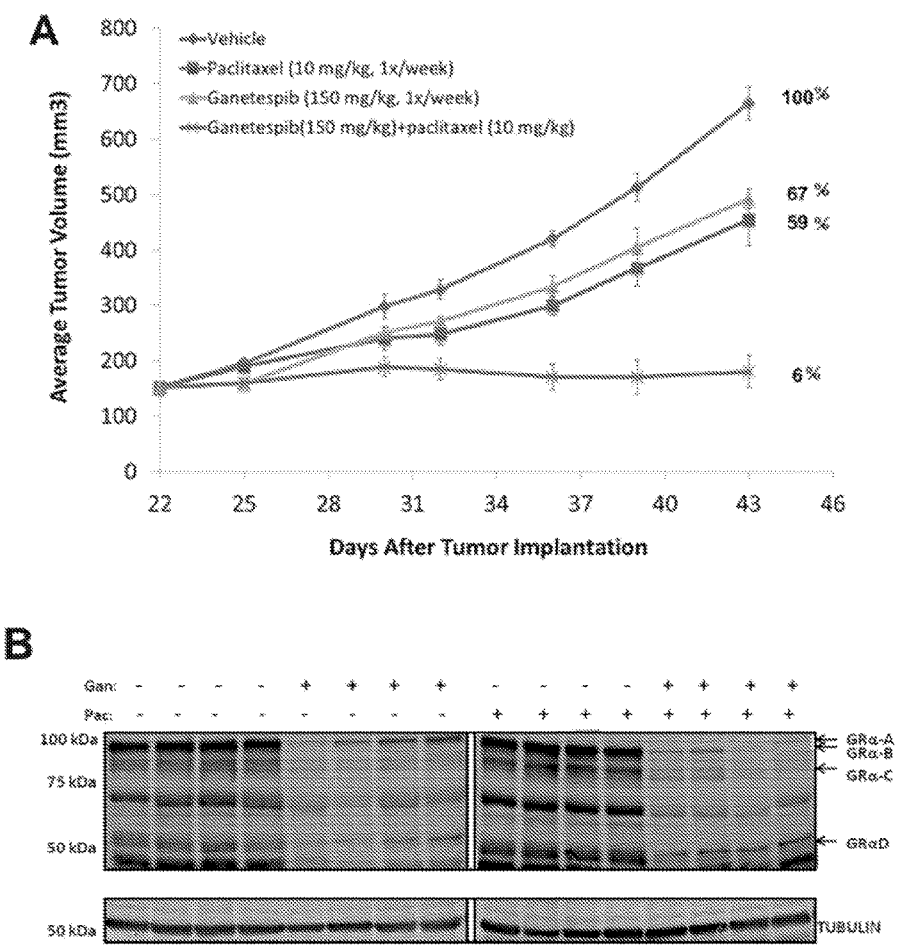
FIGS. 8A-8B.

Addition of an Hsp90 Inhibitor to Paclitaxel Leads to Increased Cell Death and GR Depletion In Vivo FIG. 8A shows a GR+ MDA-MB-231 xenograft study showing efficacy of paclitaxel (pac, 10 mg/kg) and ganetespib (gan, 150 mg/kg) compared to either agent alone. FIG. 8B shows the GR protein levels in the same tumors treated in FIG. 8A.

Example 7

Hsp90 inhibitor treatment of TNBC cells results in proteasome-mediated degradation of GR and AR.
GR and AR transcriptional activity is decreased following Hsp90 inhibitor treatment.
Addition of Hsp90 inhibitor to paclitaxel leads to increased cell death in vitro and in vivo.
GR expression is required for increased cell death following addition of an Hsp90 inhibitor to paclitaxel in vitro.

Example 8

GR expression is determined to be required for increased tumor cell death following addition of Hsp90 inhibitor to paclitaxel in vivo by establishing GR knockdown TNBC xenografts.
GR overexpression in GR-depleted cells is required for Hsp90 inhibitor-mediated sensitization of TNBC cells to paclitaxel.

Example 9

The multiplex RT-PCR assay was performed to discover GR target genes that are affected by HSP90 inhibitor treatment of a triple-negative breast cancer cell line, MDA-MB-231.

| Well | Gene name Activated by dex and repressed by gan | Veh/Veh | Dex/Veh | Dex/Gan |
|---|---|---|---|---|
| A05 | Hs.9613 NM_001039667 ANGPTL4 Angiopoietin-like 4 | 1 | 8.5 | 3.5 |
| A11 | Hs.478588 NM_001706 BCL6 B-cell CLL/lymphoma 6 | 1 | 2.6 | 1.1 |
| B01 | Hs.489127 NM_001742 CALCR CALCITONIN RECEPTOR | 1 | 4.3 | 2.1 |
| B03 | Hs.517106 NM_005194 CEBPB CCAAT/enhancer binding protein (C/EBP), beta | 1 | 4.1 | 1.2 |
| B10 | Hs.523012 NM_019058 DDIT4 DNA-damage-inducible transcript 4 | 1 | 2.9 | 0.9 |
| B12 | Hs.171695 NM_004417 DUSP1 Dual specificity phosphatase 1 | 1 | 3.7 | 1.6 |
| C01 | Hs.511899 NM_001955 EDN1 Endothelin 1 | 1 | 2.3 | 1.6 |
| C03 | Hs.605445 NM_018948 ERRFI1 ERBB receptor feedback inhibitor 1 | 1 | 3.4 | 0.9 |
| C04 | Hs.407190 NM_004117 FKBP5 FK506 binding protein 5 | 1 | 15.5 | 5.4 |
| C08 | Hs.518525 NM_002065 GLUL Glutamate-ammonia ligase | 1 | 1.5 | 1.3 |
| D04 | Hs.709210 NM_000565 IL6R Interleukin 6 receptor | 1 | 1.9 | 1.4 |
| D05 | Hs.525752 NM_015995 KLF13 Kruppel-like factor 13 | 1 | 2.5 | 1.6 |
| D06 | Hs.150557 NM_001206 KLF9 Kruppel-like factor 9 | 1 | 9.5 | 2.4 |
| D07 | Hs.102267 NM_002317 LOX Lysyl oxidase | 1 | 2.4 | 1.5 |
| D09 | Hs.534330 NM_175617 MT1E Metallothionein 1E | 1 | 2.7 | 1.3 |
| D10 | Hs.647371 NM_005953 MT2A Metallothionein 2A | 1 | 3.0 | 2.1 |
| D11 | Hs.81328 NM_020529 NFKBIA Nuclear factor of kappa light polypeptide gene enhancer in B-cells inhibitor, alpha | 1 | 2.0 | 0.9 |
| E04 | Hs.445534 NM_002616 PER1 Period homolog 1 (*Drosophila*) | 1 | 12.7 | 2.5 |
| F01 | Hs.502876 NM_004040 RHOB Ras homolog gene family, member B | 1 | 5.6 | 1.3 |
| F03 | Hs.591336 NM_014454 SESN1 Sestrin 1 | 1 | 1.4 | 1.1 |
| F04 | Hs.510078 NM_005627 SGK1 Serum/glucocorticoid regulated kinase 1 | 1 | 2.9 | 1.4 |
| F06 | Hs.30246 NM_006996 SLC19A2 Solute carrier family 19 (thiamine transporter), member 2 | 1 | 2.0 | 1.3 |
| F07 | Hs.443572 NM_003060 SLC22A5 Solute carrier family 22 (organic cation/carnitine transporter), member 5 | 1 | 1.3 | 0.9 |

-continued

| Well | Gene name Activated by dex and repressed by gan | Veh/Veh | Dex/Veh | Dex/Gan |
|---|---|---|---|---|
| G03 | Hs.211600 NM_006290 TNFAIP3 Tumor necrosis factor, alpha-induced protein 3 | 1 | 2.2 | 1.2 |
| G04 | Hs.716410 NM_004089 TSC22D3 TSC22 domain family, member 3 | 1 | 22.8 | 3.4 |
| G05 | Hs.524085 NM_171997 USP2 Ubiquitin specific peptidase 2 | 1 | 3.1 | 2.3 |
| G09 | Hs.250 NM_000379 XDH Xanthine dehydrogenase | 1 | 1.3 | 1.1 |
| G10 | Hs.534052 NM_003407 ZFP36 Zinc finger protein 36, C3H type, homolog (mouse) | 1 | 4.3 | 1.3 |

REFERENCES

The following references, to the extent that they provide exemplary procedural or other details supplementary to those set forth herein, are specifically incorporated herein by reference. Belanoff et al., *Eur. J. Pharmacol.*, 655(1-3):117-20, 2011.

Cho et al. *Biochemistry*, 44(9):3547-61, 2005.
Clark, *Curr. Top. Med. Chem.* 8(9):813-838, 2008.
Colleoni et al., *Annals of Oncology*, 11(8):1057, 2000.
Echeverria P C et al. (2010), Molecular chaperones, essential partners of steroid hormone receptors for activity and mobility, Biochim Biophys Acta, 1803:641-9, 2010.
Euopean Appln. EP 373 203
Euopean Appln. EP 785 280
Euopean Appln. EP 799 897
Evans, *Science*, 240:889, 1988.
Fodor et al., *Science*, 251:767-777, 1991.
Grover and Martin, *Carcinogenesis*, 23(7):1095-102, 2002.
Hacia et al., *Nature Genet.*, 14:441-449, 1996.
Harrison's Principles of Internal Medicine, Kasper et al. (Eds.), 16th Ed., Chapter 70, 2005.
Henderson et al. *Cancer Res.*, 48:246-253, 1988.
Keen and Davidson, *Cancer*, 97(3 Suppl):825-33, 2003.
Lehmann, B D et al. (2011), Identification of human triple-negative breast cancer subtypes and preclinical models for selection of targeted therapies, Journal of Clinical Investigation 121, 2011.
Ma et al., *J. Immunol.*, 171(2):608-615, 2003.
MacBeath and Schreiber, *Science*, 289(5485):1760-3, 2000.
McNamara, K M et al. *Cancer Sci.* 104, 639-646, 2013.
Melhem et al, *Clin. Cancer Res.*, 15(9):3196-204, 2009.
Mikosz et al., *J. Biol. Chem.*, 276:16649-54, 2001.
Moran et al., *Cancer Res.*, 60:867-872, 2000.
Pan, D et al. *Cancer Res.*, 71, 6360-6370, 2011.
Pandey and Mann, *Nature*, 405(6788):837-46, 2000.
Pang and Conzen, *Cancer Biol. Ther. Cancer Biol. Ther.*, 5(8):933-40, 2006.
PCT Appln. WO 01/38580
PCT Appln. WO 01/68255
PCT Appln. WO 03/020898
PCT Appln. WO 03/022421
PCT Appln. WO 03/023058
PCT Appln. WO 03/029485
PCT Appln. WO 03/040410
PCT Appln. WO 03/053586
PCT Appln. WO 03/066906
PCT Appln. WO 03/067217
PCT Appln. WO 03/076928
PCT Appln. WO 03/087297
PCT Appln. WO 03/091426
PCT Appln. WO 03/093810
PCT Appln. WO 03/100012
PCT Appln. WO 03/100448A1
PCT Appln. WO 04/020085
PCT Appln. WO 04/027093
PCT Appln. WO 09/923256
PCT Appln. WO 09/936760
PCT Appln. WO 93/17126
PCT Appln. WO 95/11995
PCT Appln. WO 95/21265
PCT Appln. WO 95/21944
PCT Appln. WO 95/35505
PCT Appln. WO 96/30347
PCT Appln. WO 96/31622
PCT Appln. WO 96/33980
PCT Appln. WO 97/10365
PCT Appln. WO 97/27317
PCT Appln. WO 9743450
PCT Appln. WO 99/35505
Pease et al., *Proc. Natl. Acad. Sci. USA*, 91:5022-5026, 1994.
Peeters et al., *Ann. NY Acad. Sci.*, 1148:536-41, 2008.
Pike et al., *Epidemiologic Revi.*, 15(1):17-35, 1993.
Proia D A et al. (2013), Clin Cancer Res. In Press 20(2): 413-24, 2014.
Robinson, J L et al. (2011), EMBO J 30, 3019-3027, 2011.
Shoemaker et al., *Nature Genetics*, 14:450-456, 1996.
Sims et al. *BMC Medical Genomics*, 1(42):1-14, 2008.
Skor M N et. al. (2013), Glucocorticoid receptor antagonism as a novel therapy for triple-negative breast cancer, Clin Cancer Res. In Press 19(22):6163-72, 2013.
Sorlie et al., *Proc. Natl. Acad. Sci. USA*, 98:10869-10874, 2001.
Srinivas et al., *Clin. Chem.*, 48(8):1160-9, 2002.
U.S. Pat. No. 5,143,854
U.S. Pat. No. 5,202,231
U.S. Pat. No. 5,242,974
U.S. Pat. No. 5,288,644
U.S. Pat. No. 5,324,633
U.S. Pat. No. 5,384,261
U.S. Pat. No. 5,405,783
U.S. Pat. No. 5,412,087
U.S. Pat. No. 5,424,186
U.S. Pat. No. 5,429,807
U.S. Pat. No. 5,432,049
U.S. Pat. No. 5,436,327
U.S. Pat. No. 5,445,934
U.S. Pat. No. 5,468,613
U.S. Pat. No. 5,470,710
U.S. Pat. No. 5,472,672
U.S. Pat. No. 5,492,806
U.S. Pat. No. 5,503,980
U.S. Pat. No. 5,510,270
U.S. Pat. No. 5,525,464
U.S. Pat. No. 5,525,464

U.S. Pat. No. 5,527,681
U.S. Pat. No. 5,529,756
U.S. Pat. No. 5,532,128
U.S. Pat. No. 5,545,531
U.S. Pat. No. 5,547,839
U.S. Pat. No. 5,554,501
U.S. Pat. No. 5,556,752
U.S. Pat. No. 5,561,071
U.S. Pat. No. 5,571,639
U.S. Pat. No. 5,580,726
U.S. Pat. No. 5,580,732
U.S. Pat. No. 5,593,839
U.S. Pat. No. 5,599,672
U.S. Pat. No. 5,599,695
U.S. Pat. No. 5,610,287
U.S. Pat. No. 5,624,711
U.S. Pat. No. 5,631,134
U.S. Pat. No. 5,639,603
U.S. Pat. No. 5,654,413
U.S. Pat. No. 5,658,734
U.S. Pat. No. 5,661,028
U.S. Pat. No. 5,665,547
U.S. Pat. No. 5,667,972
U.S. Pat. No. 5,695,940
U.S. Pat. No. 5,700,637
U.S. Pat. No. 5,744,305
U.S. Pat. No. 5,800,992
U.S. Pat. No. 5,807,522
U.S. Pat. No. 5,830,645
U.S. Pat. No. 5,837,196
U.S. Pat. No. 5,847,219
U.S. Pat. No. 5,871,928
U.S. Pat. No. 5,876,932
U.S. Pat. No. 5,919,626
U.S. Pat. No. 6,004,755
U.S. Pat. No. 6,087,102
U.S. Pat. No. 6,368,799
U.S. Pat. No. 6,383,749
U.S. Pat. No. 6,617,112
U.S. Pat. No. 6,638,717
U.S. Pat. No. 6,720,138
U.S. Patent Pubin. 2010/0135956
UK Appln. 8 803 000
Wu et al., *Cancer Res.*, 64:1757-64, 2004.
Wu et al., *J. Clin. Invest.*, 114:560-568, 2004.
Wu et al., *Mol Endocrinol.*, 2006

The invention claimed is:

1. A method of treating breast cancer, comprising administering to a patient determined to have breast cancer cells that are chemo-resistant or not chemo-sensitive an effective amount of a combination of an Hsp90 inhibitor followed by or at the same time with at least one apoptosis-inducing agent, wherein the patient has been determined to have breast cancer cells that are glucocorticoid receptor positive ($GR^+$) and androgen receptor positive ($AR^+$).

2. The method of claim 1, wherein the patient has been determined to have cancer cells that do not express detectable levels of any of estrogen receptor, progesterone receptor, and Her2/neu.

3. The method of claim 1, wherein at least one apoptosis inducing agent is radiation, a chemotherapeutic, or an immunotherapy.

4. The method of claim 1, wherein the patient was previously administered a first apoptosis inducing agent more than two weeks prior to the Hsp90 inhibitor.

5. The method of claim 4, wherein the patient has cancer cells that were determined to be resistant to apoptosis at the time of administration of the first apoptosis inducing agent.

6. The method of claim 1, wherein the patient is determined to have cancer cells that are resistant to apoptosis.

7. The method of claim 1, wherein the apoptosis inducing agent is administered within 1 week of the Hsp90 inhibitor.

8. The method of claim 1, wherein the Hsp90 inhibitor is administered up to three days prior to administering the apoptosis inducing agent.

9. The method of claim 1, wherein the breast cancer is an unresectable breast cancer.

10. The method of claim 1, wherein the determination of $GR^+$ status comprises determining the expression of one or more GR-responsive genes selected from the group consisting of MCL1, SAP30, SMARCA2, PTGDS, TNFRSF9, SFN, LAPTM5, GPSM2, SORT1, DPT, NRP1, ACSL5, BIRC3, NNMT, IGFBP6, PLXNC1, SLC46A3, C14orf139, PIAS1, IDH2, SERPINF1, ERBB2, PECAM1, LBH, ST3GAL5, IL1R1, BIN1, WIPF1, TFPI, FN1, FAM134A, NRIP1, RAC2, SPP1, PHF15, BTN3A2, SESN1, MAP3K5, DPYSL2, SEMA4D, STOM, MAOA, ANGPTL4 (Angiopoietin-like 4), BCL6 (B-cell CLL/lymphoma 6), CALCR (CALCITONIN RECEPTOR), CEBPB (CCAAT/enhancer binding protein (C/EBP), beta), DDIT4 (DNA-damage-inducible transcript 4), DUSP1 (Dual specificity phosphatase 1), EDN1 (Endothelin 1, ERRFI1 (ERBB receptor feedback inhibitor 1), FKBP5 (FK506 binding protein 5), GLUL (Glutamate-ammonia ligase), IL6R (Interleukin 6 receptor), KLF13 (Kruppel-like factor 13), KLF9 (Kruppel-like factor 9), LOX (Lysyl oxidase), MT1E (Metallothionein 1E), MT2A (Metallothionein 2A), NFKBIA (Nuclear factor of kappa light polypeptide gene enhancer in B-cells inhibitor), alpha, PER1 (Period homolog 1 (*Drosophila*)), RHOB (Ras homolog gene family, member B), SESN1 (Sestrin 1), SGK1 (Serum/glucocorticoid regulated kinase 1), SLC19A2 (Solute carrier family 19 (thiamine transporter), member 2), SLC22A5 (Solute carrier family 22 (organic cation/carnitine transporter), member 5), TNFAIP3 (Tumor necrosis factor, alpha-induced protein 3), TSC22D3 (TSC22 domain family, member 3), USP2 (Ubiquitin specific peptidase 2), XDH (Xanthine dehydrogenase), or ZFP36 (Zinc finger protein 36, C3H type, homolog (mouse)).

11. The method of claim 1, wherein the determination of $GR^+$ status comprises measuring the expression of one or more GR-responsive genes or GR in one or more circulating tumor cells.

12. The method of claim 1 further comprising:
a) administering radiation or a chemotherapeutic to the patient after the patient has been administered an effective amount of a combination of an Hsp90 inhibitor followed by or at the same time with at least one apoptosis-inducing agent.

13. The method of claim 1, wherein the patient has been determined to have breast cancer cells that do not express detectable levels of any of estrogen receptor, progesterone receptor, and Her2/neu.

14. The method of claim 1, wherein the patient was previously administered a first chemotherapeutic more than two weeks prior to the combination of anti-cancer compounds.

* * * * *